(12) United States Patent
Makihira

(10) Patent No.: US 9,468,374 B2
(45) Date of Patent: Oct. 18, 2016

(54) OPHTHALMOLOGIC APPARATUS AND CONTROL METHOD FOR THE SAME

(71) Applicant: CANON KABUSHIKI KAISHA, Tokyo (JP)

(72) Inventor: Tomoyuki Makihira, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 123 days.

(21) Appl. No.: 14/628,420

(22) Filed: Feb. 23, 2015

(65) Prior Publication Data

US 2015/0164320 A1 Jun. 18, 2015

Related U.S. Application Data

(62) Division of application No. 13/581,675, filed as application No. PCT/JP2011/055872 on Mar. 8, 2011, now Pat. No. 8,998,412.

(30) Foreign Application Priority Data

| Mar. 12, 2010 | (JP) | 2010-056545 |
| Mar. 12, 2010 | (JP) | 2010-056557 |
| Oct. 29, 2010 | (JP) | 2010-243537 |

(51) Int. Cl.
*A61B 3/14* (2006.01)
*A61B 3/113* (2006.01)
(Continued)

(52) U.S. Cl.
CPC .............. *A61B 3/113* (2013.01); *A61B 3/12* (2013.01); *G06T 7/0016* (2013.01); *G06T 7/204* (2013.01); *G06T 2207/30041* (2013.01); *G06T 2207/30101* (2013.01)

(58) Field of Classification Search
CPC .......... A61B 3/14; A61B 3/12; A61B 3/102; A61B 3/113; A61B 3/13

USPC ....... 351/210, 209, 206, 246, 205, 221, 212, 351/214
See application file for complete search history.

(56) References Cited

U.S. PATENT DOCUMENTS

| 7,789,511 B2 | 9/2010 | Aoki et al. |
| 8,356,898 B2* | 1/2013 | Ono ..................... A61B 3/14 351/206 |

(Continued)

FOREIGN PATENT DOCUMENTS

| CN | 101133943 A | 3/2008 |
| EP | 1 775 545 A2 | 4/2007 |

(Continued)

OTHER PUBLICATIONS

Jun. 2, 2015 Chinese Official Action in Chinese Patent Appln. No. 201180013700.9.

(Continued)

*Primary Examiner* — Hung Dang
(74) *Attorney, Agent, or Firm* — Fitzpatrick, Cella, Harper & Scinto

(57) ABSTRACT

A fundus imaging apparatus for acquiring a fundus image; and a measurement unit that extracts a characteristic image of a fundus image from a first fundus image captured by the fundus imaging apparatus, detects the characteristic image from a second fundus image that is different from the fundus image, and measures a position change in the fundus images from coordinates of the extracted characteristic image and the detected characteristic image in the respective fundus images, wherein a region in which the characteristic image is detected from the second fundus image is determined so that a region searched for the characteristic image from the first image includes the extracted characteristic image and is broader than a range of movement of the characteristic image resulting from movements of the eye ball within measurement time.

19 Claims, 28 Drawing Sheets

(51) Int. Cl.
*G06T 7/20* (2006.01)
*G06T 7/00* (2006.01)
*A61B 3/12* (2006.01)

(56) References Cited

U.S. PATENT DOCUMENTS

| | | | |
|---|---|---|---|
| 8,939,580 B2 * | 1/2015 | Nakajima | G06K 9/00597 351/206 |
| 2002/0008848 A1 | 1/2002 | Ono | |
| 2005/0140984 A1 | 6/2005 | Hitzenberger | |
| 2005/0273185 A1 | 12/2005 | Teiwes et al. | |
| 2006/0114414 A1 | 6/2006 | McGrath et al. | |
| 2007/0195269 A1 | 8/2007 | Wei et al. | |
| 2008/0077011 A1 | 3/2008 | Azuma et al. | |
| 2008/0259275 A1 | 10/2008 | Aoki et al. | |
| 2012/0002166 A1 | 1/2012 | Tomatsu et al. | |
| 2012/0154747 A1 | 6/2012 | Makihira | |
| 2012/0229761 A1 | 9/2012 | Makihira | |
| 2012/0229762 A1 | 9/2012 | Makihira | |
| 2012/0229763 A1 | 9/2012 | Suehira et al. | |
| 2012/0229764 A1 | 9/2012 | Tomatsu et al. | |
| 2012/0229765 A1 | 9/2012 | Makihira | |
| 2013/0070988 A1 | 3/2013 | Makihira | |

FOREIGN PATENT DOCUMENTS

| | | |
|---|---|---|
| EP | 1 894 518 A1 | 3/2008 |
| JP | 10-146319 A | 6/1998 |
| JP | 2001-070247 A | 3/2001 |
| JP | 2004-313545 A | 11/2004 |
| JP | 2008-079792 A | 4/2008 |
| JP | 2010-012109 A | 1/2010 |
| JP | 2011-135933 A | 7/2011 |

OTHER PUBLICATIONS

Hideo Kawai, et al., "Eye Movement Analysis System Using Fundus Images", Pattern Recognition, Elsevier, GB, vol. 19, No. 1, Jan. 1986, pp. 77-84.

Jul. 5, 2011 International Search Report and Written Opinion in PCT/JP2011/055872.

Sep. 27, 2012 International Preliminary Report on Patentability in International Patent Appln. No. PCT/JP2011/055872.

* cited by examiner

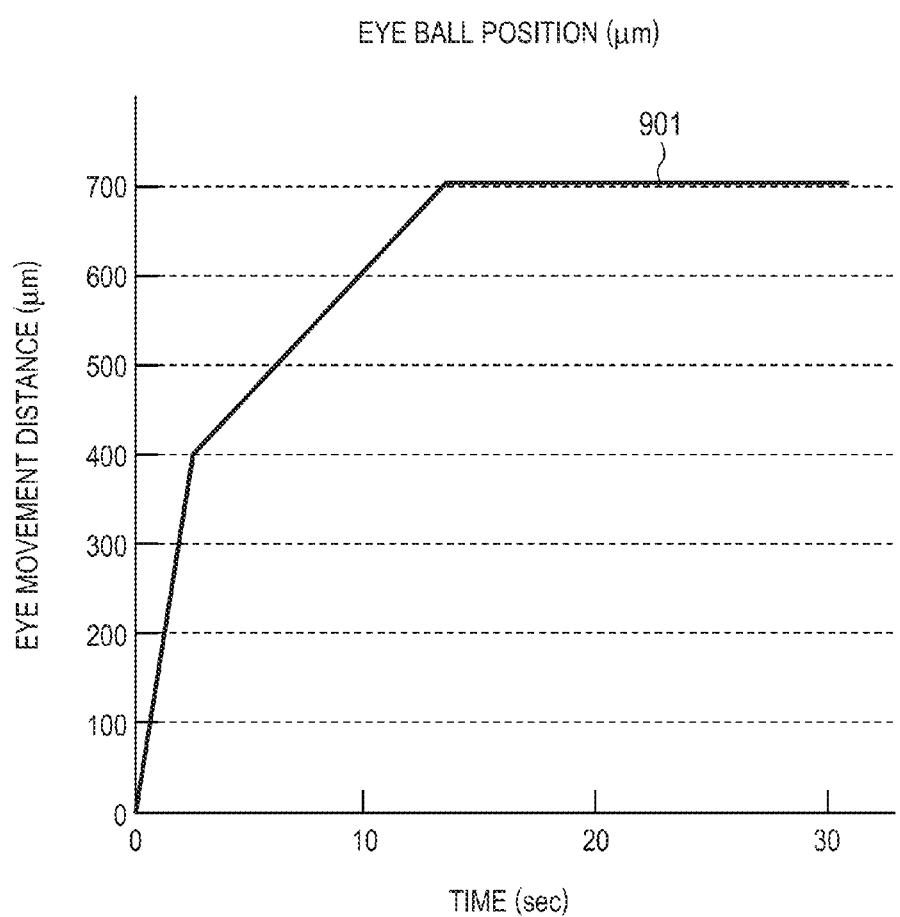

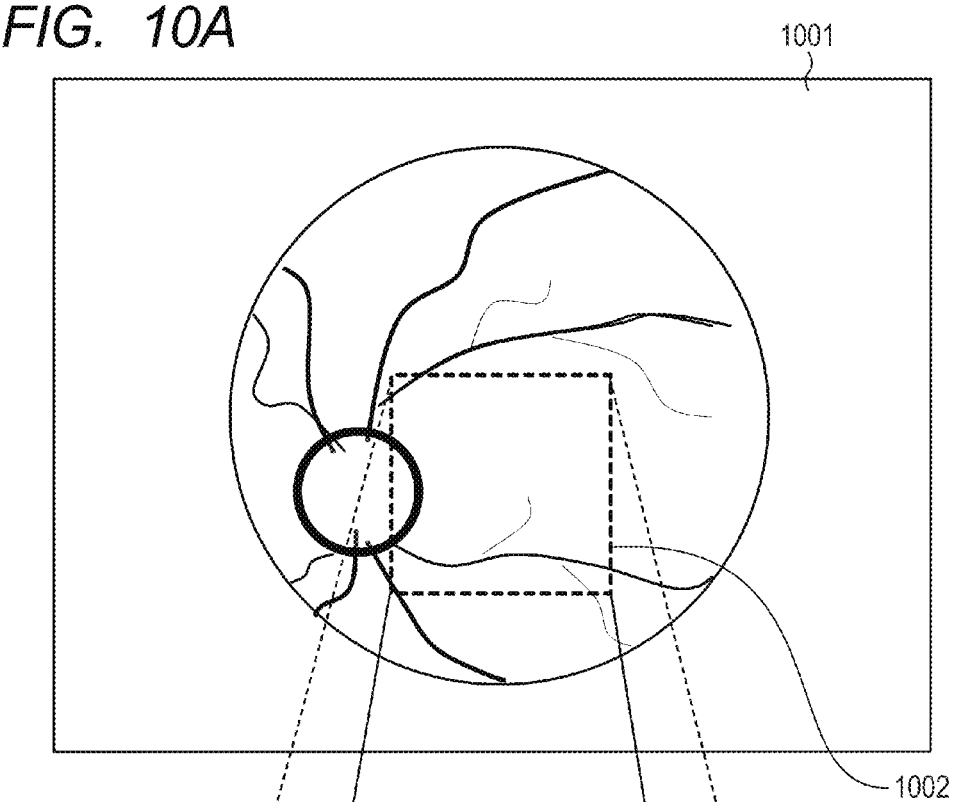
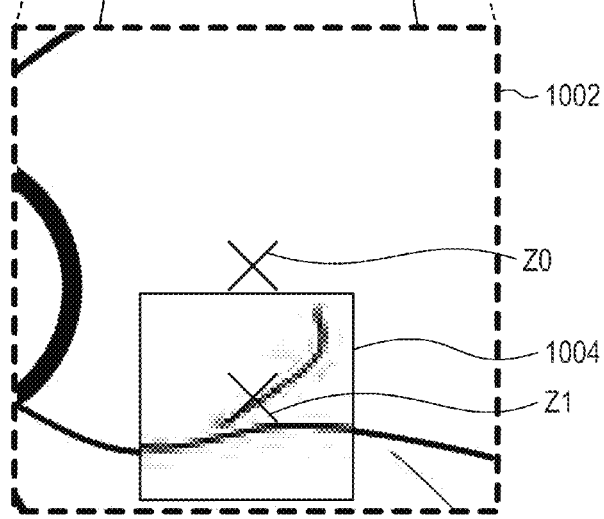

OPHTHALMOLOGIC APPARATUS AND CONTROL METHOD FOR THE SAME

This application is a division of application Ser. No. 13/581,675 filed Aug. 29, 2012, now U.S. Pat. No. 8,998,412, which was the National Stage of International Application No. PCT/JP2011/055872 filed Mar. 8, 2011.

TECHNICAL FIELD

The present invention relates to an ophthalmologic apparatus and a control method for the same, and specifically relates to an ophthalmologic apparatus in which an amount of movement of an eyeball is calculated, and a control method for the same.

BACKGROUND ART

In recent years, apparatuses that measure eye movements have attracted attention. If eye movements can be measured, such measurement can be applied to a visual field test, or, e.g., a tomographic imaging apparatus for a fundus, which acquires images with higher precision, enabling more accurate fundus diagnosis.

For eye movement measurement methods, various techniques, such as the corneal reflection (Purkinje image) method or the search coil method, have been known. Among them, a method in which eye movements are measured from fundus images has been studied as a method that is easy and less stressful for test objects.

In order to measure an eye movement with high accuracy from fundus images, it is necessary to extract a characteristic image from a fundus image, search for and detect the characteristic image in an object image and then calculate the amount of movement of the characteristic image. Among them, the step of extracting the characteristic image is important from the perspective of stability, accuracy and reproducibility of eye movement measurement. For a characteristic image in a fundus image, e.g., a macula or an optic papilla (hereinafter referred to as "papilla") is used. Also, because, e.g., an affected eye often has a defective macula or papilla, blood vessels may be used for a characteristic image in a fundus image. For a method for extracting a characteristic image of blood vessels, various methods are known. For example, Patent Literature 1 discloses a method in which the number of blood vessels and whether or not blood vessels exist in a center portion of a filter set in a fundus image are determined from average values of pixel values in an outer peripheral portion of the filter to determine whether or not a blood vessel crossing part exists in the filter region.

CITATION LIST

Patent Literature

PTL 1: Japanese Patent Application Laid-Open No. 2001-70247

SUMMARY OF INVENTION

Technical Problem

Using a method as in Patent Literature 1, a characteristic image of a fundus is extracted, and the positions of the characteristic image are compared between images to calculate the amount of movement of the eyeball between the acquired images, which enables the amount of movement of the eyeball to be detected with high accuracy from the fundus images.

However, in such method, the entire areas of the acquired fundus images are searched to extract characteristic images to be compared.

Accordingly, a problem arises in that the image processing is unnecessarily time consuming. Furthermore, another problem arises in that where an extracted characteristic image is located at an edge portion of an acquired image, the characteristic image may fall outside a processing-object image due to a movement of the eyeball, resulting in impossibility of detecting the amount of movement of the eyeball (i.e. characteristic image search error). Furthermore, when detection of a rotational movement of an eyeball is intended, if a characteristic image is extracted from a center portion of an image, no change is caused in position of the characteristic image resulting from the rotation of the eyeball, which may result in impossibility of detecting the rotation.

Solution to Problem

In order to solve the aforementioned problems, an ophthalmologic apparatus for detecting an amount of a movement of an eye to be inspected, according to a first configuration of the present invention includes: an image acquiring unit that acquires a plurality of fundus images of the eye to be inspected, at different times; a processing unit that sets a partial region from at least one fundus image from among the plurality of acquired fundus images, based on an eye movement amount performs processing, the processing being at least one of extraction and search of at least one characteristic image for the set partial region; and a detecting unit that detects a position change in the plurality of fundus images based on a result of the processing performed by the processing unit.

A method for detecting an amount of movement of an eye to be inspected, according to a second configuration of the present invention, includes the steps of: acquiring a plurality of fundus images of the eye to be inspected, at different times; performing processing including extraction of a characteristic image from each of at least two fundus images from among the plurality of acquired fundus images and calculation of a coordinate difference between the extracted characteristic images; detecting a position change in the plurality of fundus images based on a result of the processing; and setting a partial region for at least one fundus image from among the plurality of acquired fundus images, based on an eye movement amount.

Advantageous Effects of Invention

According to the present invention, a region matching a characteristic image can efficiently and reliably be found within a processing-object image, enabling an increase in speed of template matching.

Further features of the present invention will become apparent from the following description of exemplary embodiments with reference to the attached drawings.

BRIEF DESCRIPTION OF DRAWINGS

FIG. 9 is a schematic diagram of a graph relating to eye movements and time in the present invention.

FIG. 10A is a schematic diagram relating to template matching in example 1 of the present invention.

FIG. 10B is a schematic diagram relating to template matching in example 1 of the present invention.

DESCRIPTION OF EMBODIMENTS

Modes for setting a partial region according to the present invention will be described in details in the following examples with reference to the drawings. Examples 1 to 3 will be described in terms of an example where in a fundus image acquiring apparatus, a characteristic image in a fundus image is extracted, and then a region to be searched for the extracted characteristic image within another object image is adjusted, thereby enhancing the processing speed. Examples 4 to 6 will be described in terms of an example where when extracting a characteristic image in a fundus image, an extracting region is designated, enabling more efficient and reliable eye movement measurement.

Although the below examples will be described in terms of an example where the present invention is applied to a single apparatus, the subject matter of the present invention is not limited to any of the configurations described below, and is either not limited to a single apparatus including any of the configurations described below. The present invention can be provided by use of a method for providing functions described below, and processing for supplying software (computer program) providing such functions to a system or an apparatus via a network or various types of recording media and causing a computer (or, e.g., a CPU or a MPU) in the system or the apparatus to read and execute the program.

Example 1

Hereinafter, example 1 of the present invention will be described.

Fundus Imaging Apparatus

Figure 1:
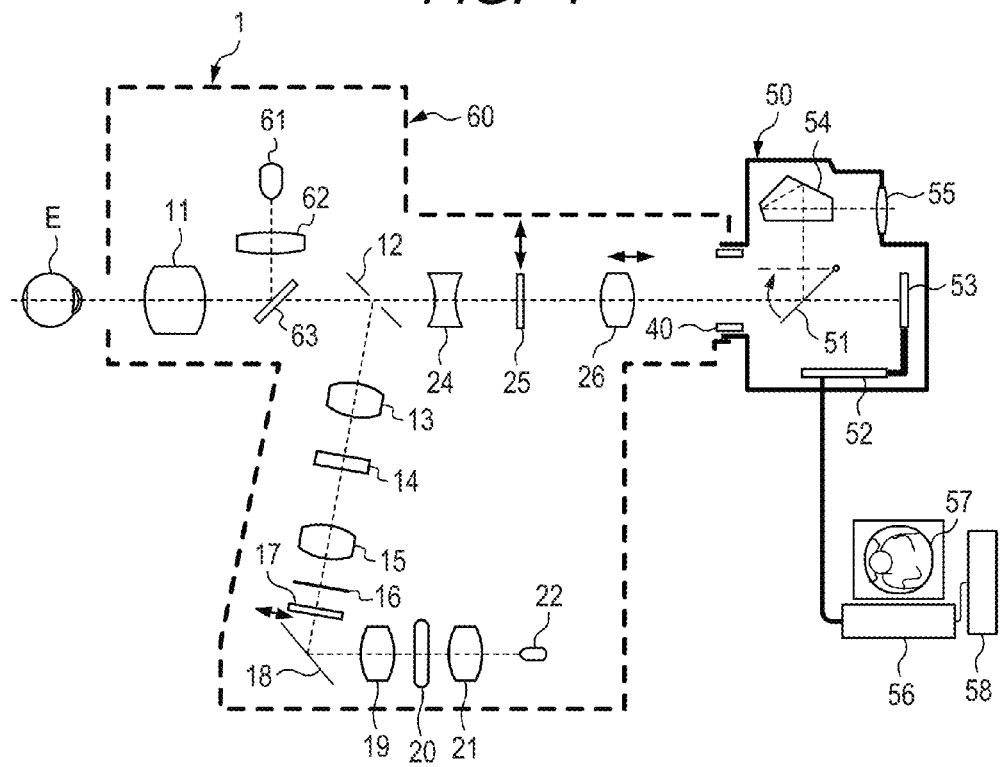
FIG. 1 is a schematic diagram illustrating a configuration of an optical system of a fundus camera in example 1 of the present invention.

A fundus camera used for fundus imaging in the present example will be described. FIG. 1 illustrates a schematic diagram of a fundus camera. A digital single-lens reflex camera 50 that can perform imaging at a video rate is connected to a fundus camera body portion 1 via a connection unit 40 as a signal acquisition unit. A perforated mirror 12 is provided on an optical path of an object lens 11 facing an eye (E) to be inspected. On an optical path on the incident side of the perforated mirror 12, a relay lens 13, a black point plate 14, a relay lens 15, a ring slit plate 16, a fluorescent exciter filter 17 and a mirror 18 are arranged. Furthermore, on the incident side of the mirror 18, a condenser lens 19, a shooting light source 20 including a xenon tube, a condenser lens 21, and an observation light source 22 including an infrared light emitting diode are arranged. The optical paths in the Figure are indicated by dotted lines.

Behind the perforated mirror 12, a focusing lens 24, a fluorescence barrier filter 25 and an image-forming lens 26 are arranged, and the digital single-lens reflex camera 50 is connected thereto. In the digital single-lens reflex camera 50, a quick-return mirror 51, a focal plane shutter (not illustrated) and a two-dimensional sensor 53 are arranged on an optical path that is the same as an optical path behind the object lens 11. Also, on the reflection side of the quick return mirror 51, a pentaprism 54 and an ocular lens 55 are provided. Signals received by the two-dimensional sensor 53 are processed in a signal processing board 52, transferred via a cable to a PC 56 including an HDD 58, and displayed on a display 57. In the fundus camera body portion 1, an internal fixation lamp unit 60 is provided, and light emitted from a light source 61 of an internal fixation lamp is reflected by a dichroic mirror 63 via a lens 62 and applied to the eye to be inspected. A unit for stabilizing fixation is not limited to this, and for example, an external fixation lamp (not illustrated) may be provided. In the fundus camera body portion 1, a non-illustrated control device is provided, and the control device controls the overall fundus camera while communicating with the PC 56.

Control Method

Figure 2:
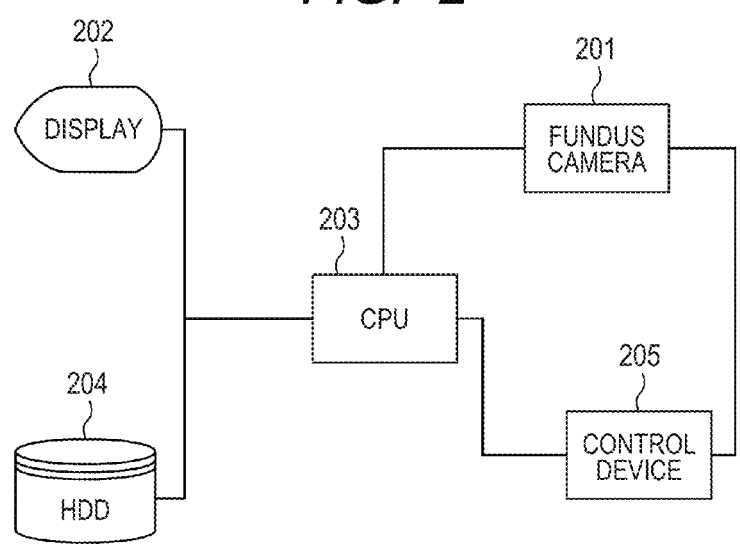
FIG. 2 is a schematic diagram of a functional architecture of an apparatus in example 1 of the present invention.

FIG. 2 illustrates a functional architecture used in the present example. The functional architecture includes a CPU 203 that controls the overall system, a control device 205 that controls the fundus camera, a fundus camera 201 that acquires fundus images, a display 202 that displays a system status, and an HDD (recording unit) 204 that records, e.g., fundus images and/or imaging conditions. At the time of observation and shooting of a fundus, imaging conditions are provided from the CPU 203 to the control device 205 and a fundus is imaged. After the imaging of the fundus, the image is sent from the fundus camera 201 to the CPU 203 where, e.g., image processing is performed, and then displayed in the display 202 and simultaneously or subsequently stored in the recording unit 204.

Figure 3:
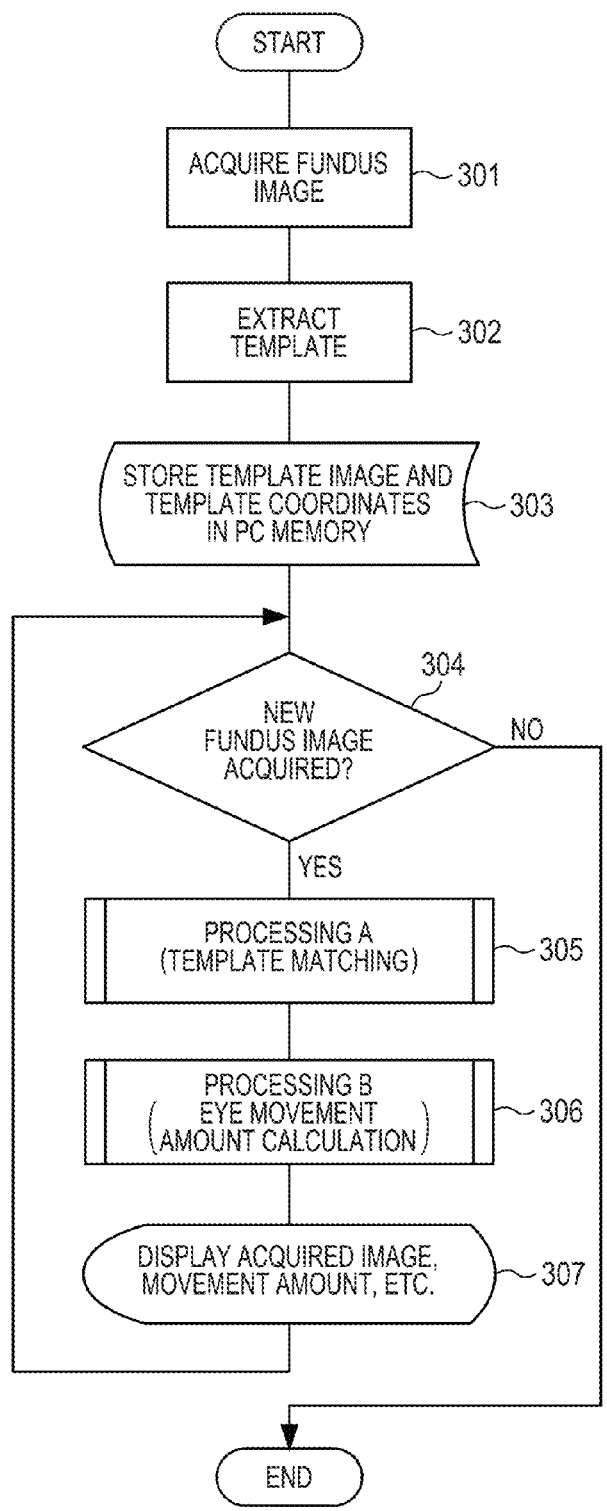
FIG. 3 is a flowchart of a control flow in example 1 of the present invention.

FIG. 3 illustrates an overall flow of measuring eye movements for a period of time using the above-described functions. A fundus image is acquired using the fundus camera 1 (step 301). After the acquisition of the fundus image, a characteristic image (hereinafter referred to as "template image") is extracted via the PC 56 (step 302). The template image and template coordinates, which are reference coordinates of the template image, are stored in the recording unit 204 (step 303). Here, template coordinates can be values of center coordinates of a template image where a reference position is an origin (0, 0), and means information on a position of the template image relative to the reference position (first position information). Since the fundus camera successively performs imaging for the period of time, upon acquisition of a following new fundus image (step 304), in processing A (step 305), the acquired image is searched by the PC 56 for the template image (hereinafter referred to as "template matching") and the amount of eye movements for the period of time is calculated by processing B (step 306). The eye movement amount, the image, measurement time, a real-time monitor image of an anterior eye part, etc., are displayed (step 307). The processing from steps 304 to 307 are repeated until the end of the eye movement measurement.

Figure 4:
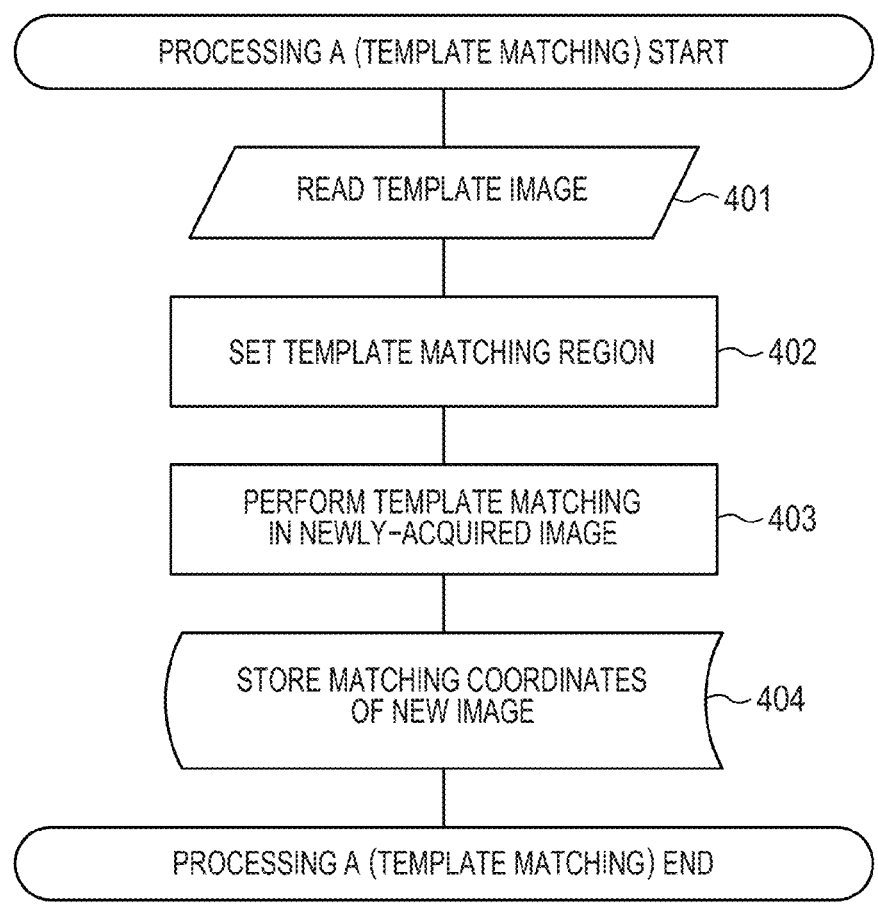
FIG. 4 is a flow chart relating to processing A in the control flow in example 1 of the present invention.

A detailed flow of template matching in processing A (step 305), which is a partial flow, will be described with reference to FIG. 4. Here, the template image stored in the recording unit 204 is read (step 401), a region for which template matching is performed is set in a newly-acquired fundus image (step 402), and template matching is performed in the newly-acquired fundus image (step 403). After the end of the template matching, reference coordinates of a matching image, that is, matching coordinates, are stored in the recording unit 204 (step 404). Here, matching coordinates are values of center coordinates of the matching image where a point in the second image corresponding to the reference position in the first image is the origin (0, 0), and means information on a position of the matching image relative to the reference position (second position information). Although in the present example, reference coordinates are center coordinates of the matched-object image, any reference coordinates such as upper left corner coordinates may be employed.

Figure 5:
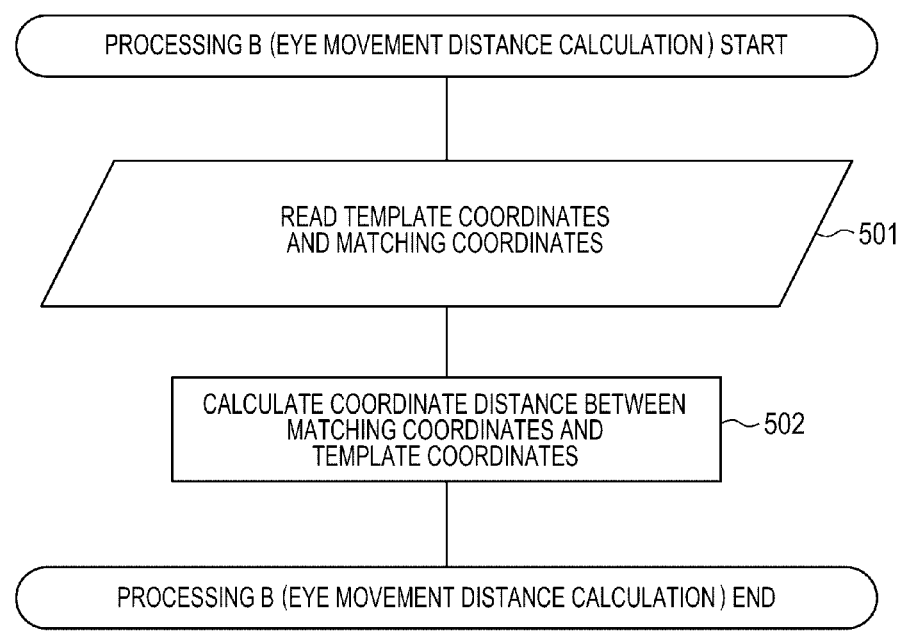
FIG. 5 is a flow diagram relating to processing B in the control flow in example 1 of the present invention.

Next, processing B (step 306) will be described with reference to FIG. 5. In processing B, first, the template coordinates and the matching coordinates are read from the recording unit 204 (step 501), the coordinate difference between the template coordinates and the matching coordinates is calculated (step 502), and the movement distance is calculated from the coordinate difference.

Tracking Measurement: Specific Example

FIGS. 6A, 6B, 6C, 6D, 6E and 6F illustrate respective images corresponding to the above-described processing. A case where tracking measurement is performed for 20 seconds using the above-described fundus camera, under measurement conditions of acquiring a fundus image with a diameter of 10 mm at a frequency of 10 Hz will be indicated as an example.

Figure 6A:
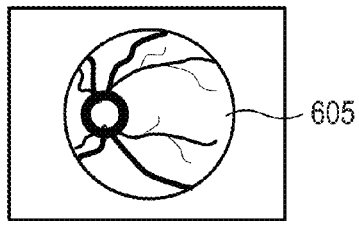
FIG. 6A is a schematic diagram illustrating a fundus image in example 1 of the present invention.
Figure 6B:
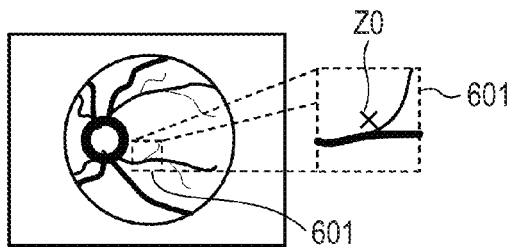
FIG. 6B is a schematic diagram illustrating a fundus image in example 1 of the present invention.
Figure 6C:
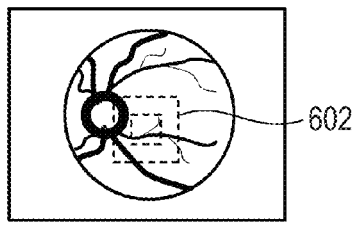
FIG. 6C is a schematic diagram illustrating a fundus image in example 1 of the present invention.
Figure 6D:
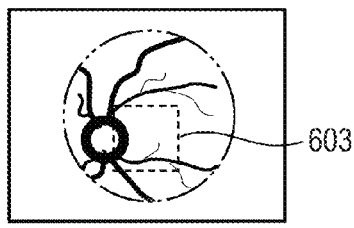
FIG. 6D is a schematic diagram illustrating a fundus image in example 1 of the present invention.
Figure 6E:
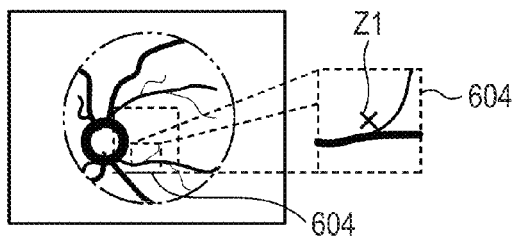
FIG. 6E is a schematic diagram illustrating a fundus image in example 1 of the present invention.
Figure 6F:
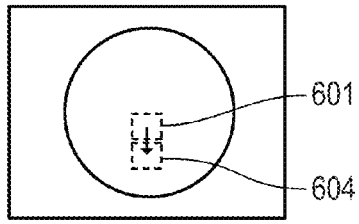
FIG. 6F is a schematic diagram illustrating a fundus image in example 1 of the present invention.

FIG. 6A illustrates an acquired first fundus image 605. As illustrated in FIG. 6A, blood vessels run intricately from a papilla toward an edge portion. After acquisition of the first fundus image, as illustrated by dotted lines in FIG. 6B, a template image 601 is extracted. Although here, a square image region of 500 µm×500 µm is employed for a template image, a template image is not limited to this and the shape and size of a template image can arbitrarily be determined. The extracted template image 601 and template coordinates Z0 are stored. In the present example, an origin (0, 0) is set for center coordinates of the fundus image 605, and center coordinates of the template image of this time is $Z_0$ (0, −200). The coordinate unit is µm. However, the coordinate setting method is also not limited to this. Next, as illustrated in FIG. 6C, a region 602 to be searched for the template image 601 when detecting the template image from the new fundus image, that is, a template matching implementing region 602 (hereinafter referred to as "matching region") is set in the first fundus image by means of the CPU 203. Here, a matching region in a second image is set with reference to the template coordinates of the template image in the first image (as the center) so that the matching region is broader than a range of movement of the region of the template image resulting from movement or rotation of the eyeball caused by, e.g., involuntary eye movements within measurement time. Next, in FIG. 6D, illustrating a second fundus image, which is a newly-acquired matching object, an extracting region 603 (first extracting region) is set at a coordinate position that is the same as that of the matching region 602 in the first fundus image. Subsequently, the extracting region 603 is searched for a region corresponding to the template image 601 (template matching). With the above-described configuration, search for a region corresponding to a template can be conducted only in an extracting region, eliminating the need to search the entire second fundus image, and thus, search time can be reduced. As illustrated in FIG. 6E, after detection of a corresponding region 604, center coordinates (matching coordinates) $Z_1$ of the image region 604 corresponding to the template image are measured. In this example, the matching coordinates $Z_1$ are (0, −400). As illustrated in FIG. 6F, using the template coordinates $Z_0$ and the matching coordinates $Z_1$, a coordinate change is figured out to calculate the eye movement amount (0 µm, −200 µm in the present example). The above-described template matching in FIGS. 6D to 6G is performed for each of newly-acquired fundus images, i.e., matching is performed on each new image acquired at a frequency of 10 Hz, and the amount of movement of the eyeball from the reference position during the measurement time is measured and displayed.

Figure 7A:
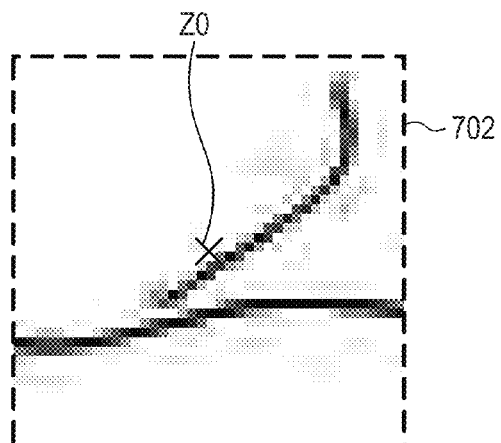
FIG. 7A is a schematic diagram relating to a matching region in example 1 of the present invention.
Figure 7B:
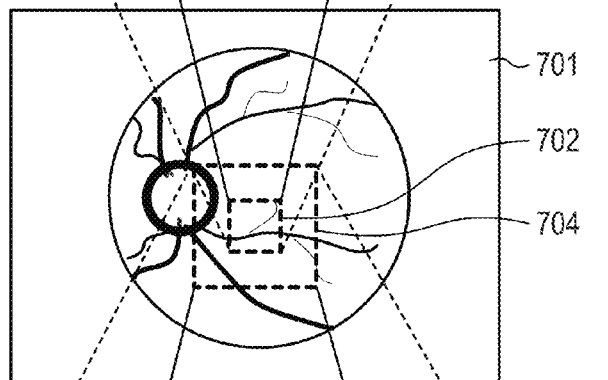
FIG. 7B is a schematic diagram relating to a matching region in example 1 of the present invention.
Figure 7C:
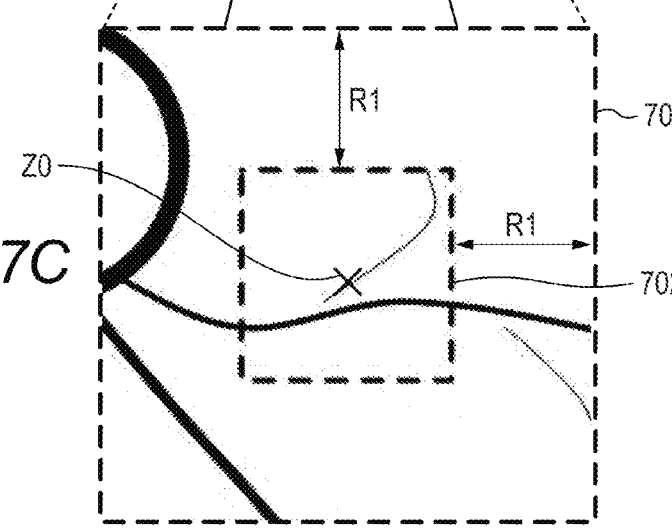
FIG. 7C is a schematic diagram relating to a matching region in example 1 of the present invention.
Figure 8:
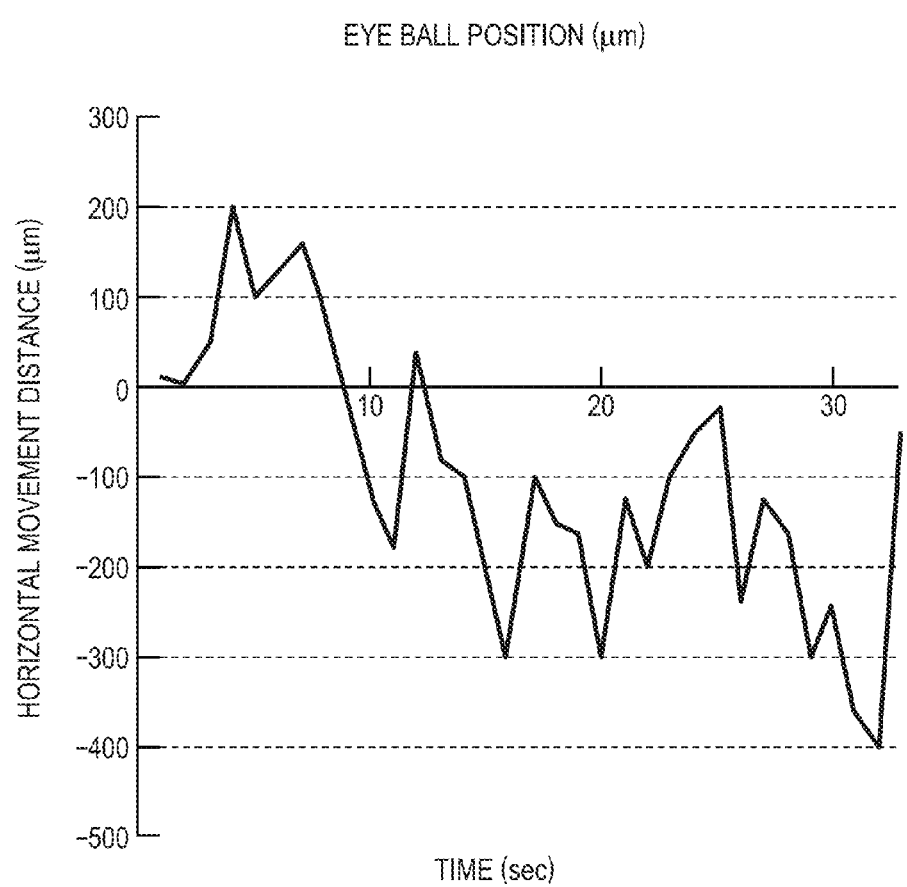
FIG. 8 is a schematic diagram illustrating eye movements in the present invention.

An example of the matching region setting method performed in FIG. 6C is indicated below. In this example, a matching region is a region including a combination of the region of a template image and the region of an area having a fixed width ($R_1$) outward from edge portions of the template image. FIG. 7B illustrates an enlarged view 701 of the fundus image 605 in FIG. 6C. FIG. 7A illustrates an enlarged view of a template image 702. FIG. 7C illustrates an enlarged view of a matching region 704. The matching region 704 is calculated considering the size and precision of the fundus image as well as attribute information such as involuntary eye movements. In the present example, the matching region 704 is a region including the region of an area within $R_1$ mm outside the template image region from the image edge portions of the template image 702, and the template image 702. Here, a value that is larger than the amount of movement of a human eye within the measurement is used for $R_1$. FIG. 8 illustrates the results of measurement of involuntary eye movements of a human eye by means of an apparatus including an internal fixation lamp. As illustrated in FIG. 8, in the case of a fixation lamp being provided, movement of a human eye caused by involuntary eye movements tends to fall within a certain distance with a fixation point as the center. FIG. 9 illustrates a modeling function between time from the start of fixation and distance of movement of a human eye, which includes the aforementioned tendency. The amount of movement of a human eye within measurement time can be figured out based on this graph. For the graph, a known graph provided in advance for each imaging condition, such as external fixation, internal fixation, affected eye or normal subject, age, or time required for capturing one fundus image, can be used, and thus, the graph can arbitrarily be selected depending on the measurement method and/or object. The present example employs measurement for 20 seconds, and according to the function, the amount of movement of the eyeball can be considered 700 µm, and accordingly, R1 is 700 µm. Thus, the matching region 704 has a size of 1.9 mm×1.9 mm.

Next, template matching will be described in detail with reference to FIGS. 10A and 10B. As illustrated in FIG. 10A, an extracting region 1002 calculated as described above is set in a newly-captured second fundus image 1001 according to the coordinates, and an enlarged view 1002 of the extracting region is searched for a template image. As illustrated in FIG. 10B, as a result of the search, a corresponding image region 1004 is detected and center coordinates $Z_1$ thereof are calculated as matching coordinates. The result of the above-described processing may be displayed on the monitor in real time or after measurement.

As described above, setting a matching region and an extracting region at the time of template matching enables an increase in speed of template matching. Also, as a result of limiting the regions, false detection can be prevented.

Example 2

Example 2 of the present invention will be described below.

Example 2 will be described in terms of a case where an SLO (scanning laser ophthalmoscope) is used for acquiring fundus images, eye movements are measured from the SLO fundus images by means of a method similar to that of example 1, and the results of measurement of the eye movements are fed back in real time to an optical coherent tomographic imaging apparatus (OCT: optical coherent tomography), thereby providing a high-precision 3D OCT image.

OCT Apparatus Configuration

In the present example, an OCT apparatus is used for an ophthalmologic apparatus. A general description of an OCT apparatus will be given with reference to FIG. 11.

For a low-coherence light source 1101, an SLD (super luminescent diode) light source or an ASE (amplified spontaneous emission) light source can preferably be used. For low-coherence light, light with wavelengths of around 850 nm and around 1050 nm is preferably used for fundus imaging. In the present example, an SLD light source with a center wavelength of 840 nm and a wavelength half width of 45 nm is used. Low-coherence light applied from the low-coherence light source 1101 enters a fiber coupler 1102 via a fiber and split into a measuring beam (also referred to "OCT beam") and a reference beam. Although the configuration of an interferometer using a fiber is described here, a spatial optical system with a configuration using a beam splitter may be employed.

The measuring beam is provided from a fiber collimator 1104 via a fiber 1103 in the form of a collimated beam. Furthermore, the measuring beam passes through an OCT scanner (Y) 1105 and relay lenses 1106 and 1107, and further through an OCT scanner (X) 1108, penetrates a dichroic beam splitter 1109, passes through a scan lens 1110, a dichroic mirror 1111 and an ocular lens 1112, and enters an eye to be inspected (e). Here, galvano scanners are used for the OCT scanners (X) 1108 and (Y) 1105. The measuring beam that has entered the eye e to be inspected is reflected by the retina and returns to the fiber coupler 1102 through the same optical path. The reference beam is guided from the fiber coupler 1102 to a fiber collimator 1113 and provided in the form of a collimated beam. The provided reference beam passes through a dispersion compensation glass 1114 and is reflected by a reference mirror 1116 on an optical length changing stage 1115. The reference beam reflected by the reference mirror 1116 returns to the fiber coupler 1102 via the same optical path.

The measuring beam and the reference beam that have returned to the fiber coupler 1102 are combined and guided to a fiber collimator 1117. Here, light resulting from the combination is called interference light. The fiber collimator 1117, a grating 1118, a lens 1119 and a line sensor 1120 are included in a spectroscope. The interference light is measured by the spectroscope in terms of information on the intensity for each wavelength. The information on the intensity for each wavelength measured by the line sensor 1120 is transferred to a non-illustrated PC and reproduced as a tomographic image of the eye to be inspected e.

SLO Configuration

Figure 11:
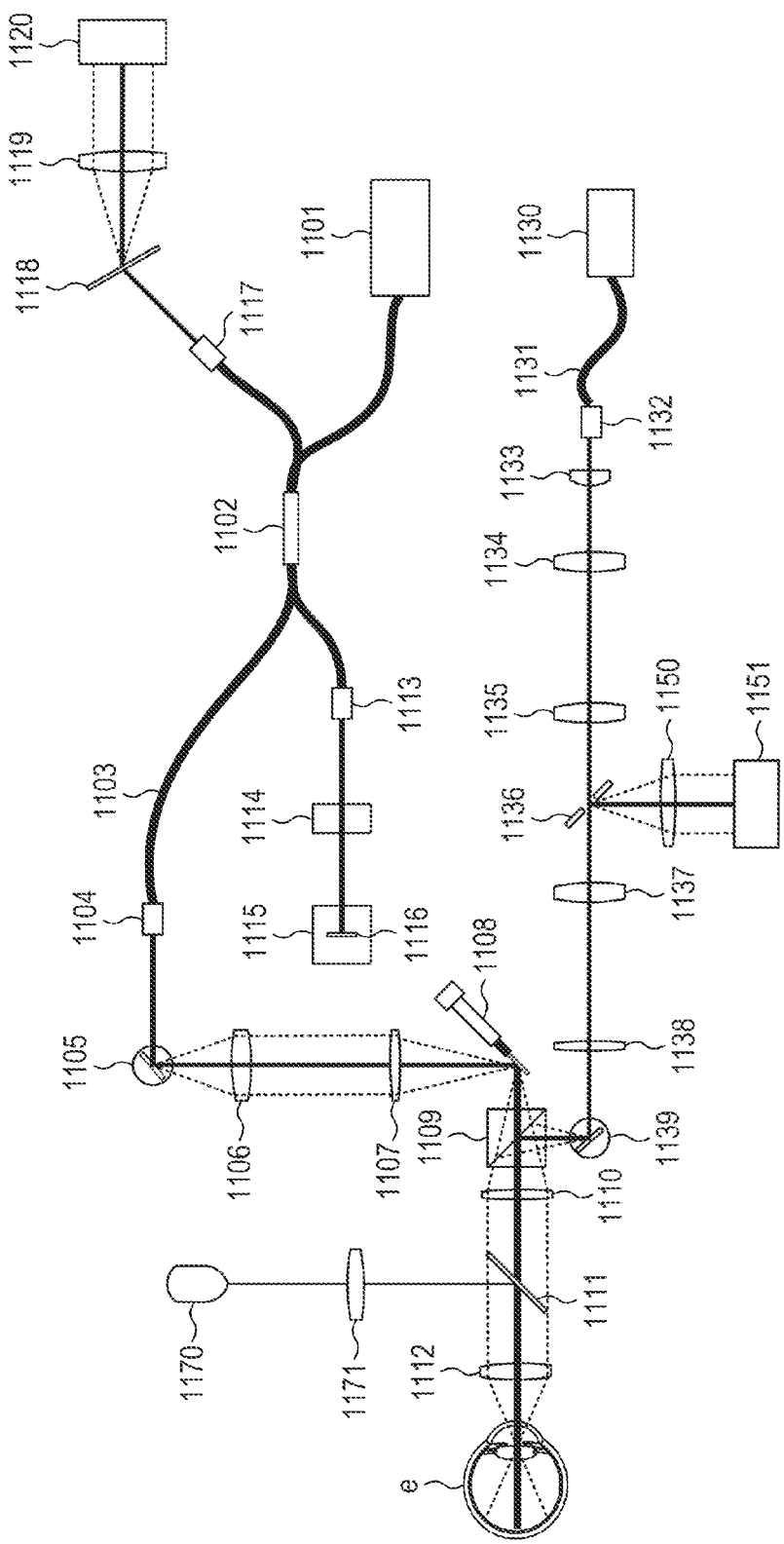
FIG. 11 is a schematic diagram illustrating configurations of optical systems in an OCT apparatus and an SLO apparatus in example 2 of the present invention.

Next, an optical configuration of an SLO imaging unit that acquires fundus images will be described also with reference to FIG. 11. For a laser light source 1130, a semiconductor laser or an SLD light source can preferably be used. There is no restriction on the wavelength to be used as long as a light source that can separate a wavelength to be used, from the wavelengths of the low-coherence light source for OCT, by means of a wavelength separation unit, is used, and a near-infrared wavelength range of 700 nm to 1000 nm is preferably used for the quality of a fundus observation image. In the present example, a semiconductor laser with a wavelength of 760 nm is used. A laser emitted from the laser light source 1130 is output from a fiber collimator 1132 via a fiber 1131 in the form of a collimated beam and enters a cylindrical lens 1133. Although the present example has been described in terms of a case where a cylindrical lens is used, there is no specific restriction as long as an optical element that can generate a line beam, and a line beam shaper using a Powell lens or a diffraction optical element can be also used. The beam that has been widened by the cylindrical lens 1133 (also referred to as "SLO beam") is made to pass through a center of a ring mirror 1136 by relay lenses 1134 and 1135, passes through relay lenses 1137 and 1138 and is guided to an SLO scanner (Y) 1139. For the SLO scanner (Y), a galvano scanner is used. The beam is further reflected by a dichroic beam splitter 1109, passes through the scan lens 1110, the dichroic mirror 1111 and the ocular lens 1112, and enters the eye e to be inspected. The dichroic beam splitter 1109 is configured so as to transmit an OCT beam and reflect an SLO beam. The SLO beam that has entered the eye to be inspected is applied to the fundus of the eye e to be inspected in the form of a line-shaped beam. The line-shaped beam is reflected or scattered by the fundus of the eye e to be inspected and returns to the ring mirror 1136 via the same optical path. The position of the ring mirror 1136 is conjugate to the position of the pupil of the eye e to be inspected, and thus, light passing through the region around the pupil in the light resulting from backscattering of the line beam applied to the fundus, is reflected by the ring mirror 1136 and forms an image on a line sensor 1151 via a lens 1150. Based on information on the intensity for each position of the line sensor 1151, a planar image of the fundus is generated by means of the non-illustrated PC. Although in the present example, an SLO with a line-scan SLO (hereinafter referred to as "L-SLO") configuration using a line beam has been described, it should be understood that a flying spot SLO may also be used.

Internal Fixation Lamp

The present example includes an internal fixation lamp that makes the eye e to be inspected be fixed thereon to stabilize involuntary eye movements. The internal fixation lamp included in the present example will be described with reference to FIG. 11 as with the OCT apparatus and the SLO apparatus. For a light source 1170 used for the fixation lamp, a light emitting diode (LED) is used. The position where the light emitting diode is lighted is changed according to the site intended to be imaged, under the control of the PC. The light emitting diode 1170 generates light with a wavelength of 500 nm, and a beam emitted from the light source is applied to the eye e to be inspected via a lens 1171 and the dichroic mirror 1111. The dichroic mirror 1111, which is positioned between the scan lens 1110 and the ocular lens 1112, separates between light with a short wavelength (around 500 nm), and an OCT beam and an SLO beam (no less than 700 nm).

Control Method

Figure 12:
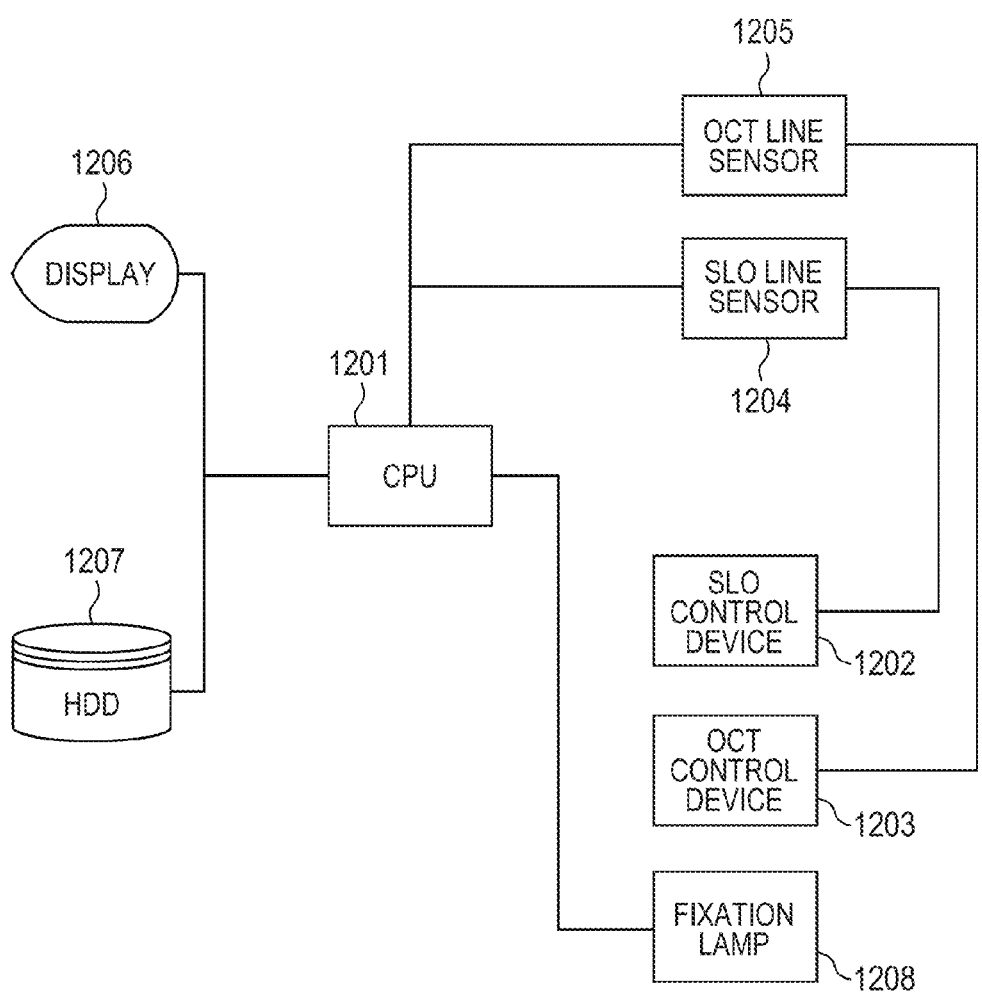
FIG. 12 is a schematic diagram of a functional architecture in an apparatus in example 2 of the present invention.

FIG. 12 illustrates a functional architecture used in the present example. The functional architecture includes: a CPU 1201 that controls the overall system; respective control devices 1202 and 1203 that control the SLO unit and the OCT unit; a fixation lamp 1208; respective cameras 1204 and 1205 that acquire SLO images and OCT images; a display 1206 in a PC, the display 1206 displaying a system status; and a recording unit 1207 in the PC, the recording unit 1207 recording, e.g., fundus images and/or imaging conditions. At the time of imaging a fundus, respective imaging conditions are provided by the CPU 1201 to the control devices 1202 and 1203 and a fundus is imaged. After the fundus being imaged, an image is sent from the camera apparatuses 1204 and 1205 to the CPU 1201, subjected to image processing and then displayed on the display 1206 and simultaneously or subsequently stored in the recording unit 1207.

Figure 13:
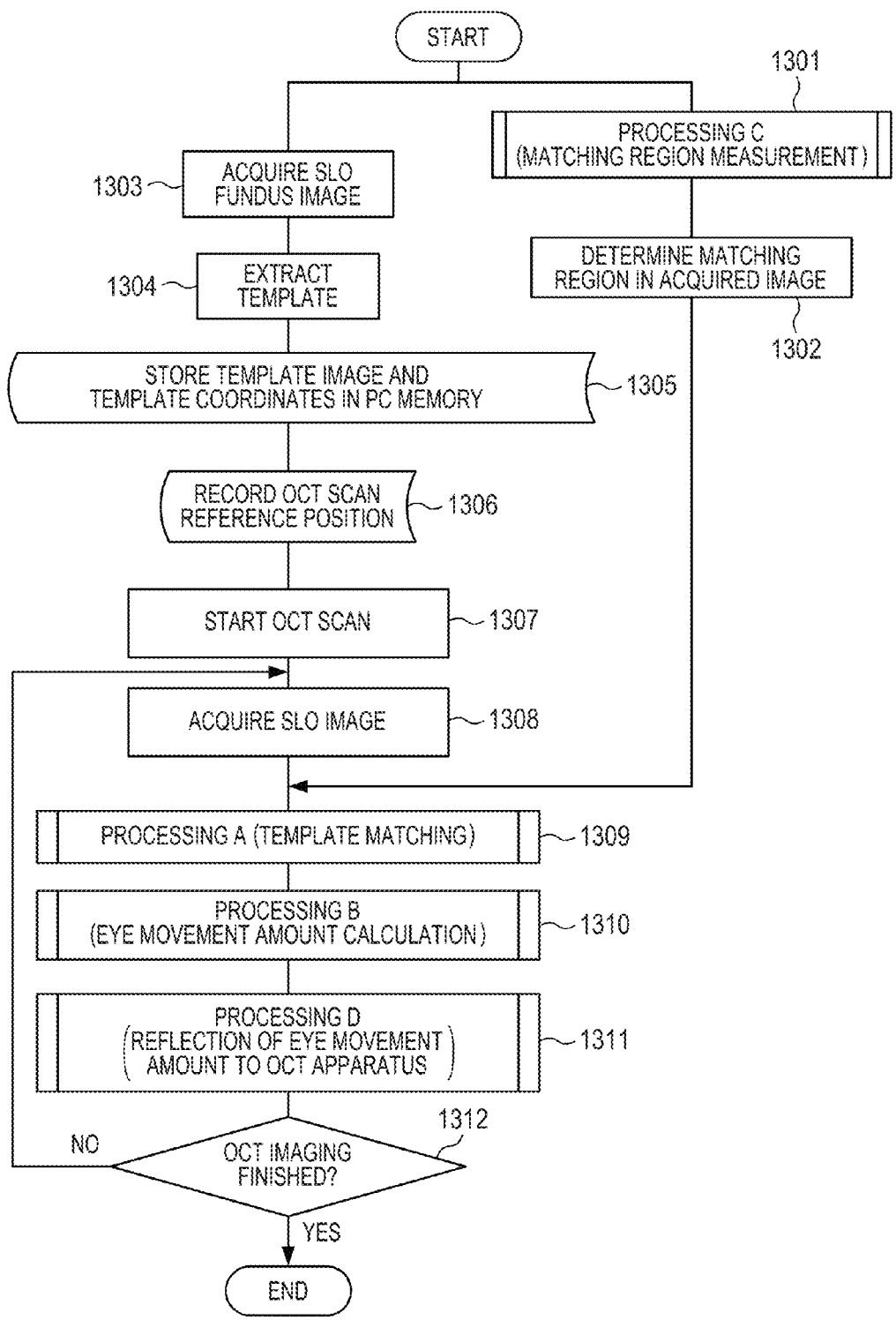
FIG. 13 is a flowchart of a control flow in example 2 of the present invention.

FIG. 13 illustrates an overall flow of measuring eye movements while acquiring tomographic images of a fundus by means of the OCT unit, using the above-described functions.

First, processing C (eye movement distance calculation) is performed (step 1301), and the width of a matching region is set by the CPU 1201 so that the matching region is broader than a range of movement of the region of a template image resulting from, e.g., involuntary eye movements during measurement time (step 1302). Independently from the above processing, the SLO unit is activated and a fundus image is acquired by means of the SLO (step 1303). A template image is extracted from the image provided by the SLO (step 1304). After the extraction of the template image, the extracted template image and coordinates thereof are stored (step 1305). A scan reference position for the OCT unit is recorded (step 1306) and the OCT unit's measurement is started (step 1307). After acquisition of a new image from the SLO unit (step 1308), as in example 1, processing A (template matching) (step 1309) and processing B (eye movement amount calculation) (step 1310) are performed, and processing D (feedback to the OCT) is performed (step 1311), and the process from steps 1308 to 1311 is repeated while the OCT unit continues measurement of tomographic images (step 1312). After the end of the OCT imaging, the measurement of eye movements is terminated (step 1313). Processing A and processing B are similar to those in example 1, and thus, a description thereof will be omitted.

Figure 14:
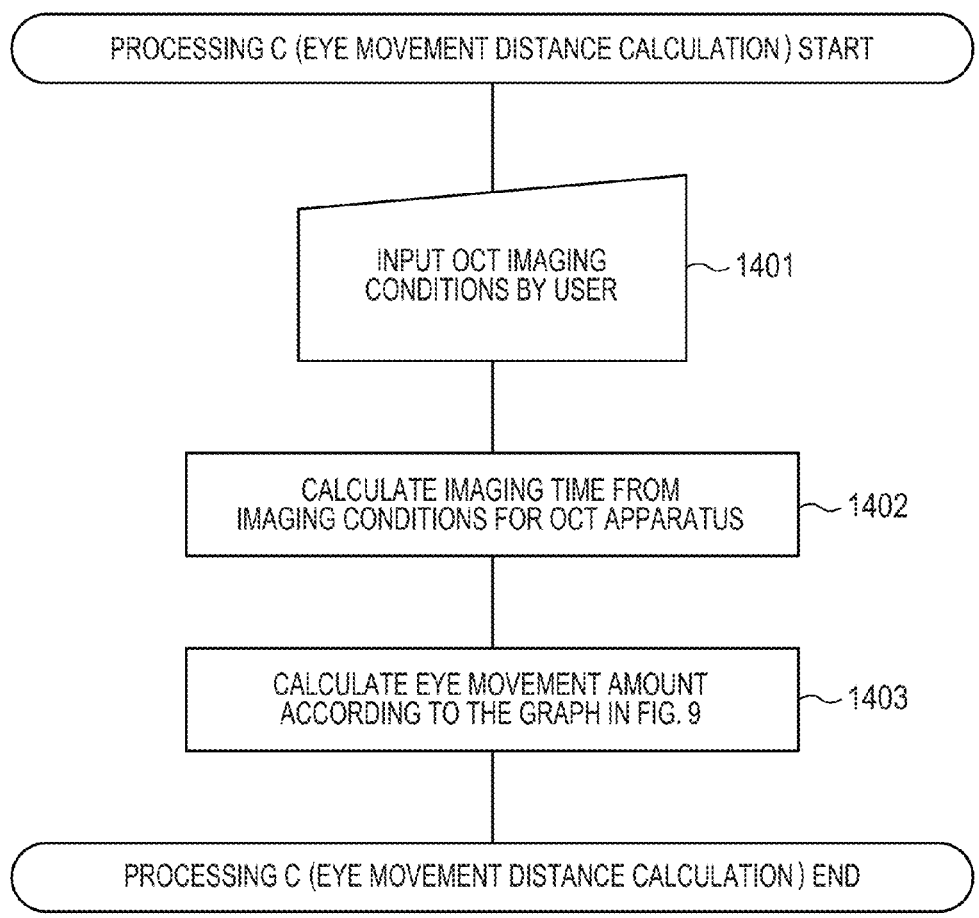
FIG. 14 is a flowchart relating to processing C in the control flow in example 2 of the present invention.

An example of processing C (eye movement distance calculation) (step 1301), which is a partial flow, will be described with reference to FIG. 14. According to OCT imaging conditions input by a user (step 1401), OCT imaging time is measured (step 1402). An eye movement distance (matching region) is calculated by applying the OCT imaging time to the graph 901 with reference to FIG. 9 (step 1403). The graph in FIG. 9 indicates eye movement amount information for a case where a normal eye is measured by an apparatus including an internal fixation lamp.

Figure 15:
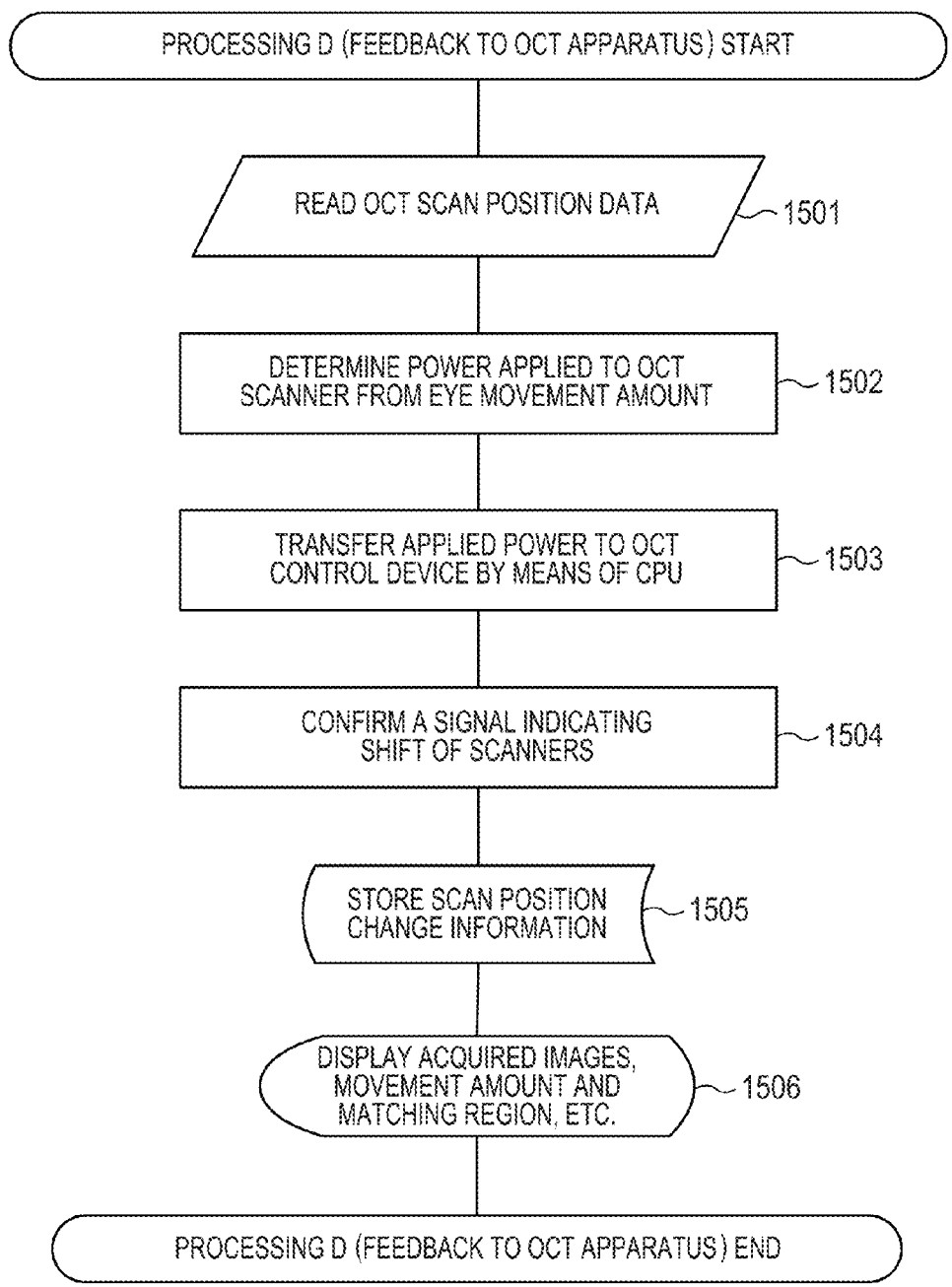
FIG. 15 is a flowchart relating to processing D in the control flow in example 2 of the present invention.

Processing D (feedback to the OCT unit) (step 1311) will be described with reference to FIG. 15. Scan position data for the OCT unit is read by the CPU 1201 (step 1501), a voltage to be applied to the OCT scanner is calculated from the eye movement amount (step 1502), the power to be applied is transferred to the OCT control device 1203 by means of the CPU 1201 (step 1503), and subsequently a signal indicating a shift of the scanners is confirmed (step 1504) and then information on the change in scan position is stored (step 1505). The change status, the OCT image, the SLO image (with indication of the matching region and the template position), the remaining time, etc., are displayed (step 1506).

Tracking Measurement: Specific Example

FIGS. 16A, 16B, 16C, 16D, 16E and 16F illustrate SLO images corresponding to the above-described processing. In the present example, the SLO has a line width of 10 mm and a scan area of 10 mm, that is, a size of an image acquired for the position of the fundus is 10 mm×10 mm. The rate of SLO image acquisition is 30 Hz. Also, the OCT unit makes the camera operate at a rate of 70 k A-scans, a B-scan image (with a fundus scan area of 10 mm and a laser spot diameter of 20 µm) includes 1000 lines, and a 3D image of a retina including 280 B-scan images is acquired. The imaging time amounts to four seconds.

Figure 16A:
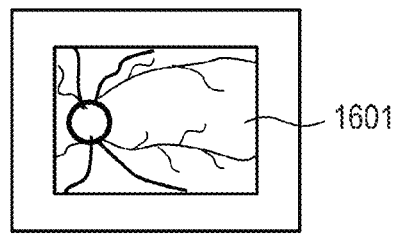
FIG. 16A is a schematic diagram illustrating an SLO fundus image in example 2 of the present invention.

First, FIG. 16A illustrates a fundus image 1601 acquired by the SLO (hereinafter simply referred to as "SLO image").

Figure 16B:
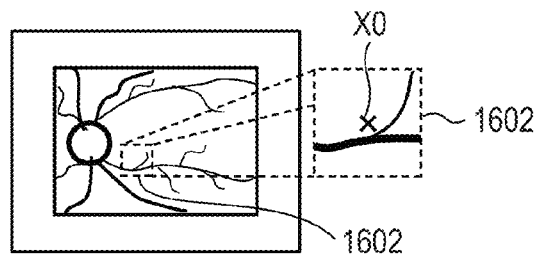
FIG. 16B is a schematic diagram illustrating an SLO fundus image in example 2 of the present invention.
Figure 16C:
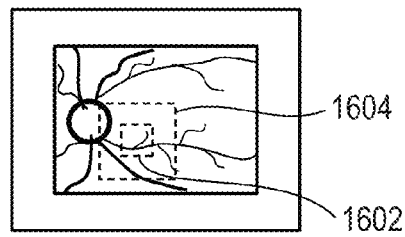
FIG. 16C is a schematic diagram illustrating an SLO fundus image in example 2 of the present invention.
Figure 16D:
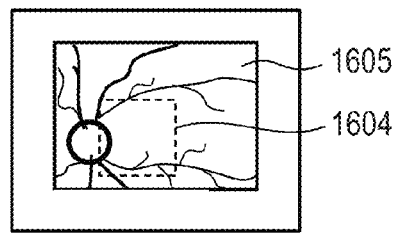
FIG. 16D is a schematic diagram illustrating an SLO fundus image in example 2 of the present invention.
Figure 16E:
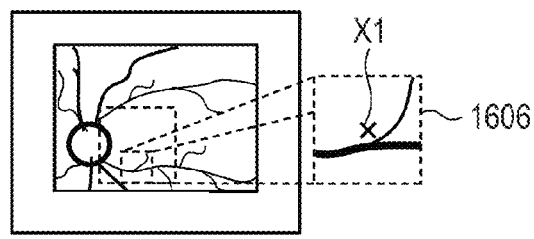
FIG. 16E is a schematic diagram illustrating an SLO fundus image in example 2 of the present invention.
Figure 16F:
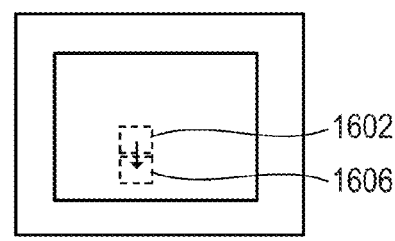
FIG. 16F is a schematic diagram illustrating an SLO fundus image in example 2 of the present invention.

As illustrated in FIG. 16A, blood vessels run intricately from a papilla toward the edges. After the acquisition of the first SLO image, the imaging time (four seconds in the present example) is calculated according to the OCT imaging conditions. Referring to FIG. 9, an eyeball moves 450 µm in four seconds. During that time, as illustrated in FIG. 16B, a template image is extracted from the first SLO image 1601. The template image 1602 and template coordinates $X_0$ (−25, −200) are stored. The coordinates have (0, 0) at the center of the SLO image. Subsequently, as illustrated in FIG. 16C, a matching region 1604 is set in consideration of an eye movement distance of 450 µm. Next, as illustrated in FIG. 16D, an extracting region 1604 is set in a newly acquired second SLO image 1605. Here, the extracting region in the second image is set with reference to the coordinates of the template image in the first image (as the center) so that the extracting region is broader than a range of movement of the region of the template image resulting from movement or rotation of the eyeball caused by, e.g., involuntary eye movements within the measurement time. Furthermore, the extracting region 1604 is searched for the template image 1602. As illustrated in FIG. 16E, after detection of a matching image 1606, center coordinates $X_1$ of the matching image 1606 are stored. Subsequently, as illustrated in FIG. 16F, the distance of movement of the eyeball is calculated from the coordinate difference between the template coordinates $X_0$ and the matching coordinates $X_1$.

Figure 17A:
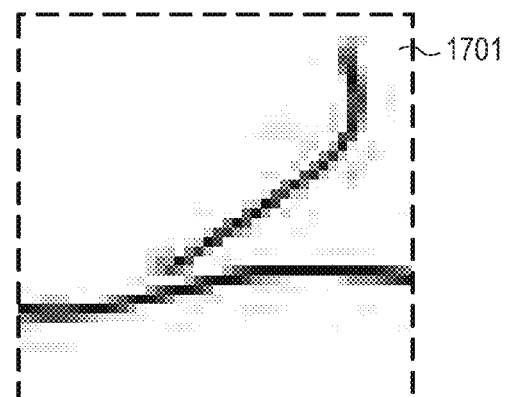
FIG. 17A is a schematic diagram relating to a matching region in example 2 of the present invention.
Figure 17B:
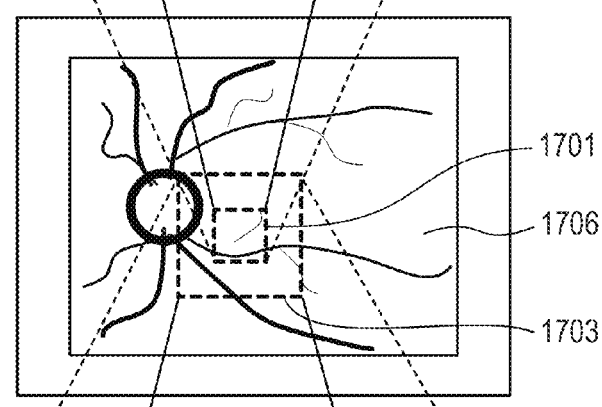
FIG. 17B is a schematic diagram relating to a matching region in example 2 of the present invention.
Figure 17C:
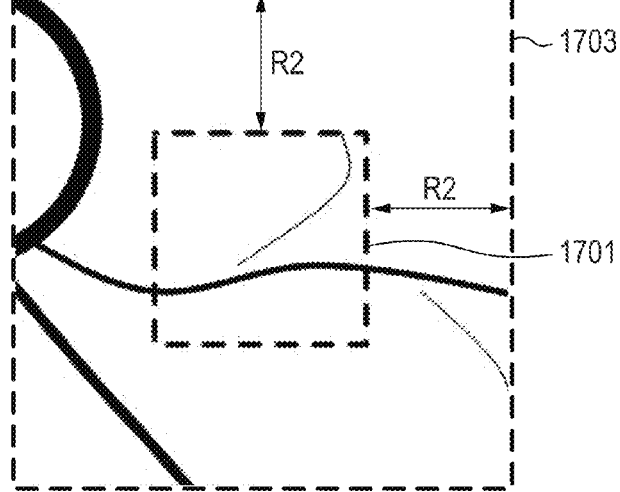
FIG. 17C is a schematic diagram relating to a matching region in example 2 of the present invention.

An example of a matching region calculation method will be described with reference to FIGS. 17A, 17B and 17C. A matching region 1703 includes a region in a SLO fundus image 1706, the region including a template image 1701 with a matching region setting width $R_2$ added thereto. As in example 1, an amount of movement of a human eye within measurement time can be figured out based on the graph in FIG. 9. For the graph, a known graph provided in advance for each imaging condition, such as external fixation, internal fixation, affected eye or normal subject, age, or time required for capturing one fundus image, can be used, and thus, the graph can arbitrarily be selected depending on the measurement method and/or subject. Among them, in example 2, the matching region setting width $R_2$ is changed according to the OCT imaging time. Since the OCT imaging time is four seconds, the eye movement distance is 450 µm according to FIG. 9. Accordingly, $R_2$ is 450 µm and the template region 1703 is a region with its respective peripheral sides extended by 450 µm in width compared to the template region 1701.

Figure 18A:
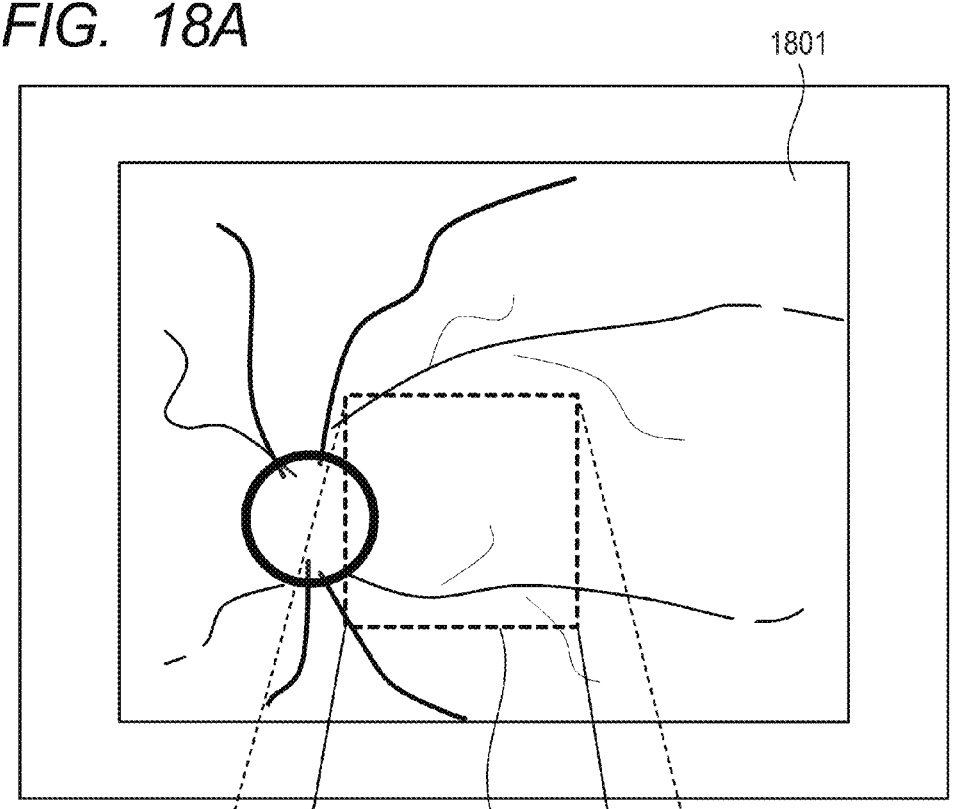
FIG. 18A is a schematic diagram relating to template matching in example 2 of the present invention.
Figure 18B:
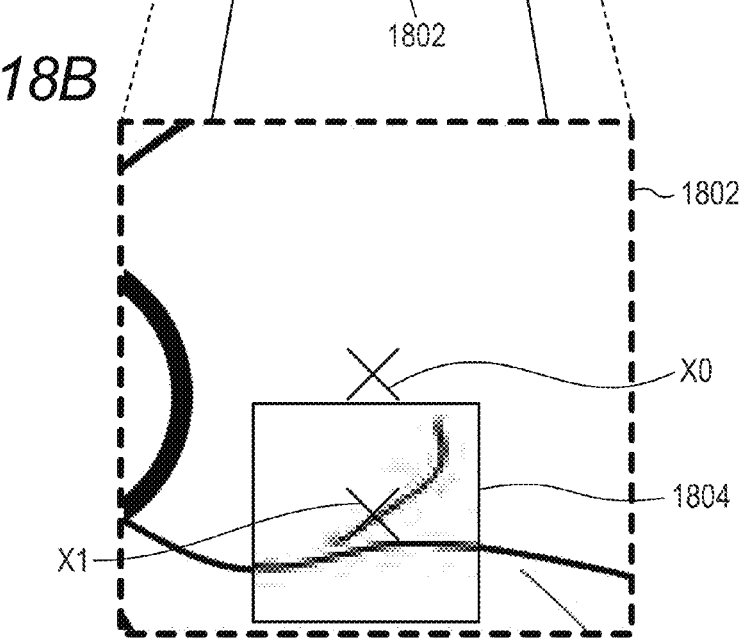
FIG. 18B is a schematic diagram relating to template matching in example 2 of the present invention.

A matching method will be described with reference to FIGS. 18A and 18B. As illustrated in FIG. 18A, an extracting region 1802 is set in a new SLO image 1801, and the extracting region 1802 is searched for a region corresponding to a template image. As illustrated in FIG. 18B, after detection of a corresponding image region 1804 corresponding to the template image, matching coordinates $X_1$ are read.

Figure 19:
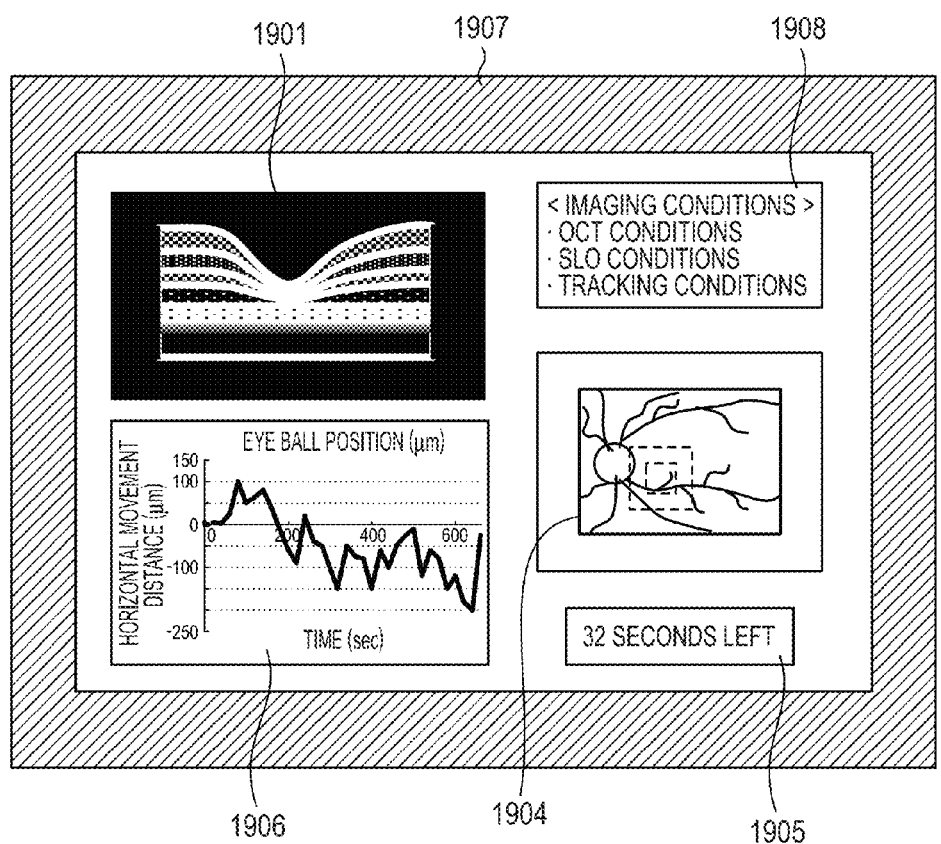
FIG. 19 is a schematic diagram indicating an example of display in example 2 of the present invention.

Here, as illustrated in FIG. 19, an OCT image 1901, eye movement measurement results 1906, remaining measurement time 1905, an SLO image (including indication of a matching region and a template image) 1904, imaging conditions 1908, etc., may be displayed on a display 1907 in a PC to enable a user to confirm the operation.

As described above, a matching region and an extracting region are set according to the OCT imaging time, enabling high-speed measurement of eye movements, and consequently, an eyeball can stably be scanned with an OCT beam, enabling acquisition of a 3D image without image displacements caused by eye movements.

Example 3

Example 3 of the present invention will be described.

As in example 2, example 3 will be described in terms of a case where an SLO (scanning laser ophthalmoscope) is used for acquiring fundus images, eye movements are measured from the SLO fundus images by means of a method that is different from those of examples 1 and 2, and the results of measurement of eye movements are fed back to an optical coherence tomographic imaging apparatus (OCT: optical coherent tomography) in real time at a higher speed, thereby providing a high-precision 3D OCT image.

The configurations of the fundus imaging apparatus (SLO) and the optical coherence tomographic imaging apparatus (OCT) are similar to those in example 2, and thus, a description thereof will be omitted. A description will be given on the flow, which is a point of difference.

Control Flow

Figure 20:
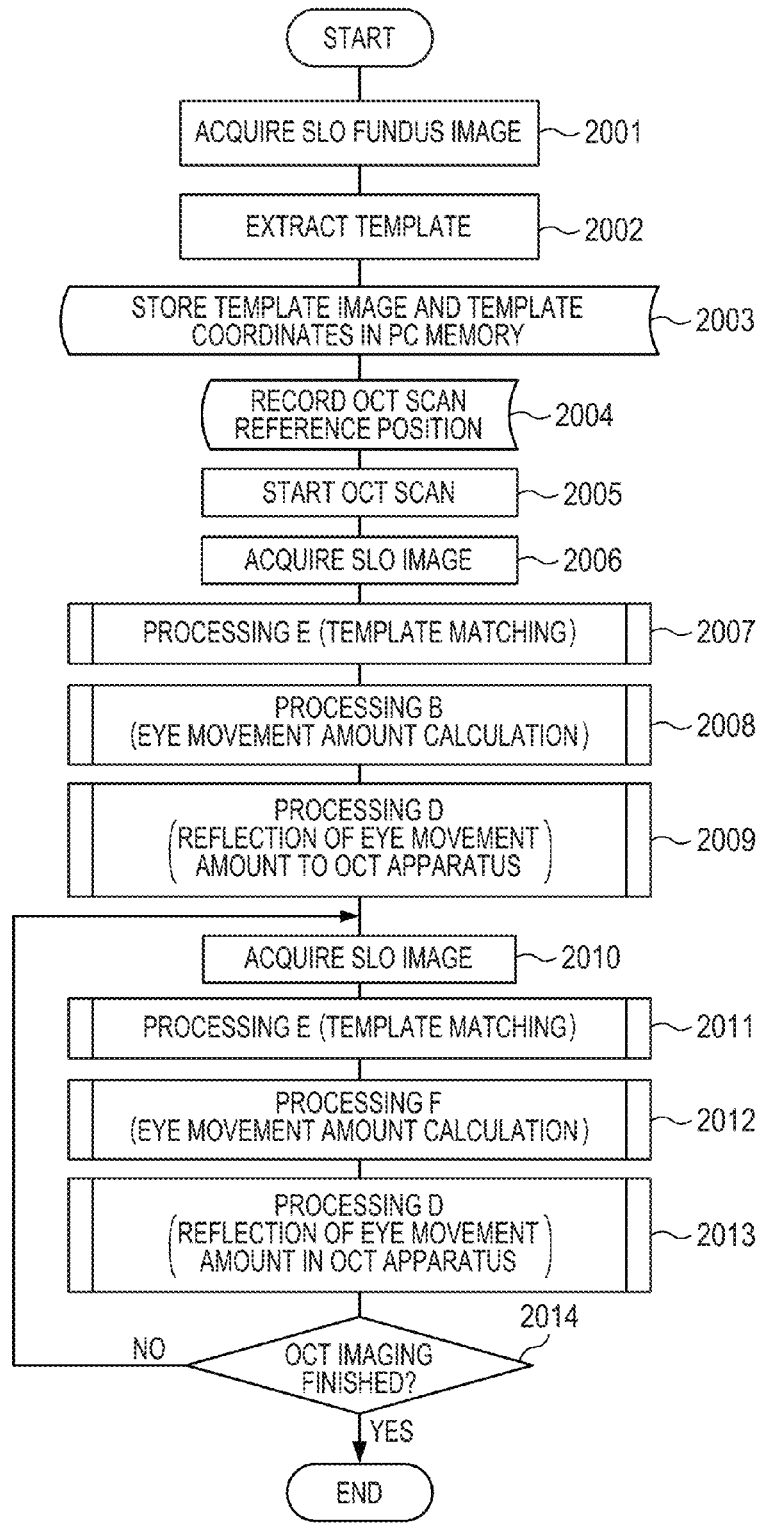
FIG. 20 is a flowchart of a control flow in example 3 of the present invention.

FIG. 20 illustrates a flowchart of an overall control flow of the present example.

First, an SLO image (first fundus image) is acquired (step 2001), a characteristic image is extracted from the acquired SLO image (step 2002), and the extracted template image and coordinates (template coordinates) thereof are stored in a recording unit (step 2003). A scan reference position of the OCT unit is recorded (step 2004), OCT imaging is started (step 2005), and simultaneously, an SLO image (second fundus image) is acquired (step 2006). Template matching (step 2007) in processing E and eye movement amount calculation (step 2008) in processing B are performed for the SLO image acquired in step 2006, and next, as in example 2, processing D (step 2009) is performed. After processing D (step 2009), an SLO image (third fundus image) is acquired again (step 2010), template matching between the template image and the SLO image in processing E (step 2011) and eye movement amount calculation for time between the acquisition of the second fundus image and the acquisition of the third fundus image in processing F (step 2012) are performed, and also in example 2, reflection of the results in the OCT apparatus in processing D (step 2013) is performed. The process from steps 2010 to 2013 is repeated until the end of the OCT imaging.

Figure 21:
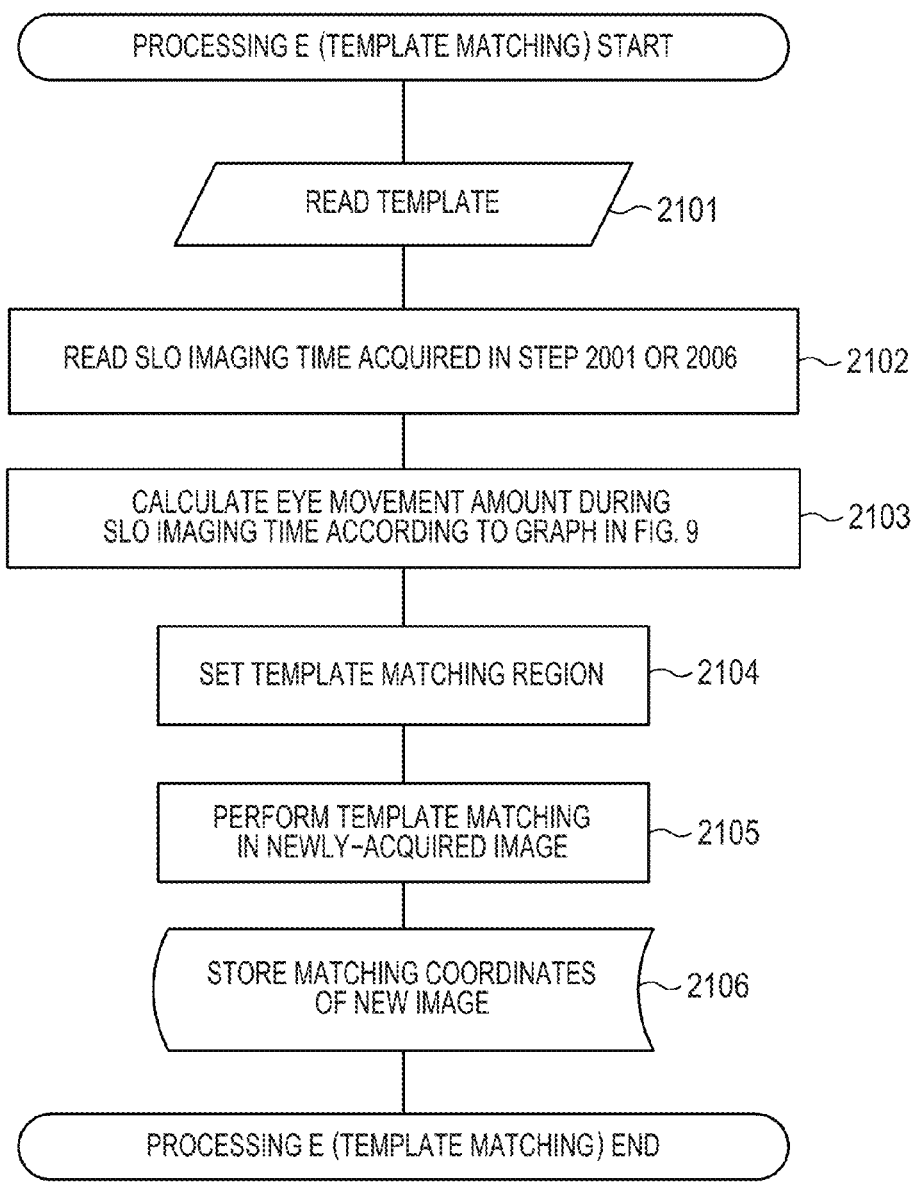
FIG. 21 is a flowchart relating to processing E in the control flow in example 3 of the present invention.

The template matching (processing E) in the present example will be described with reference to FIG. 21.

The template image extracted in step 2002 is read (step 2101), and the SLO imaging time acquired in step 2001 or 2006 is read (step 2102). The amount of movement of an eyeball during imaging is calculated according to FIG. 9 (under conditions similar to those in example 2) (step 2103). As in example 2, an extracting region (second extracting region) is set in the SLO image acquired in step 2006 or 2010, with the calculated numerical value reflected in the extracting region (step 2104). The extracting region setting method is not limited to this, and any method with a matching region set to be broader than a range of movement of the region of the template image within measurement time resulting from movement or rotation of the eyeball caused by involuntary eye movements may be employed. However, in the present example, a matching region is set based on the amount of movement of an eyeball during acquisition of one SLO image, reducing the area subjected to template matching, enabling the processing to be performed for a shorter period of time. Template matching is performed for the region set in step 2105 in the SLO image acquired in step 2006 or 2010 (step 2105), and matching information is stored (step 2106).

Figure 22:
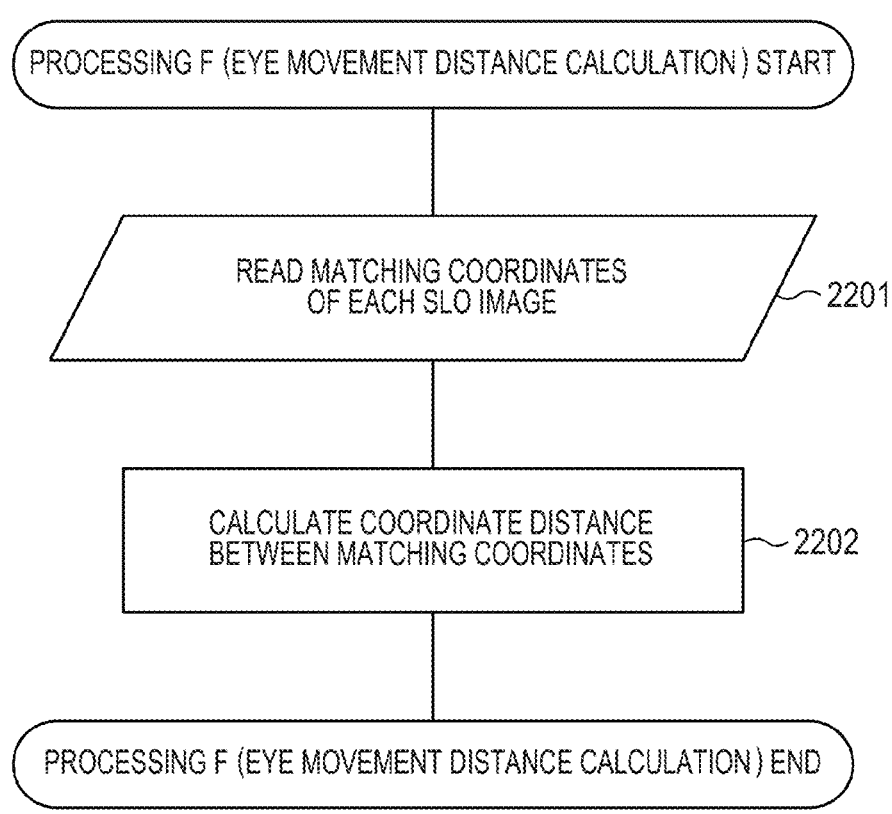
FIG. 22 is a flowchart relating to processing F in the control flow in example 3 of the present invention.

The eye movement amount calculation (processing F) in the present example will be described with reference to FIG. 22. The matching coordinates of the SLO image acquired in step 2011 and the SLO image acquired immediately before that are read (step 2201), and the coordinate difference therebetween is calculated (step 2202). The movement amount is calculated from the coordinate difference.

Specific Example

FIGS. 23A, 23B, 23C, 23D, 23E, 23F, 23G and 23H illustrate respective images corresponding to the above-described processing. As in example 2, the SLO has a line width of 10 mm and a scan area of 10 mm, that is, a size of an image acquired for the position of the fundus is 10 mm×10 mm. The rate of SLO image acquisition is 30 Hz. Also, the OCT apparatus makes a camera operate at a rate of 70 k A-scans, a B-scan image (with a fundus scan area of 10 mm and a laser spot diameter of 20 µm) includes 1000 lines, and a 3D image of a retina including 280 B-scan images is acquired. The imaging time amounts to four seconds.

Figures 23A, 23B, 23C, 23D, 23E, 23F, 23G, 23H:
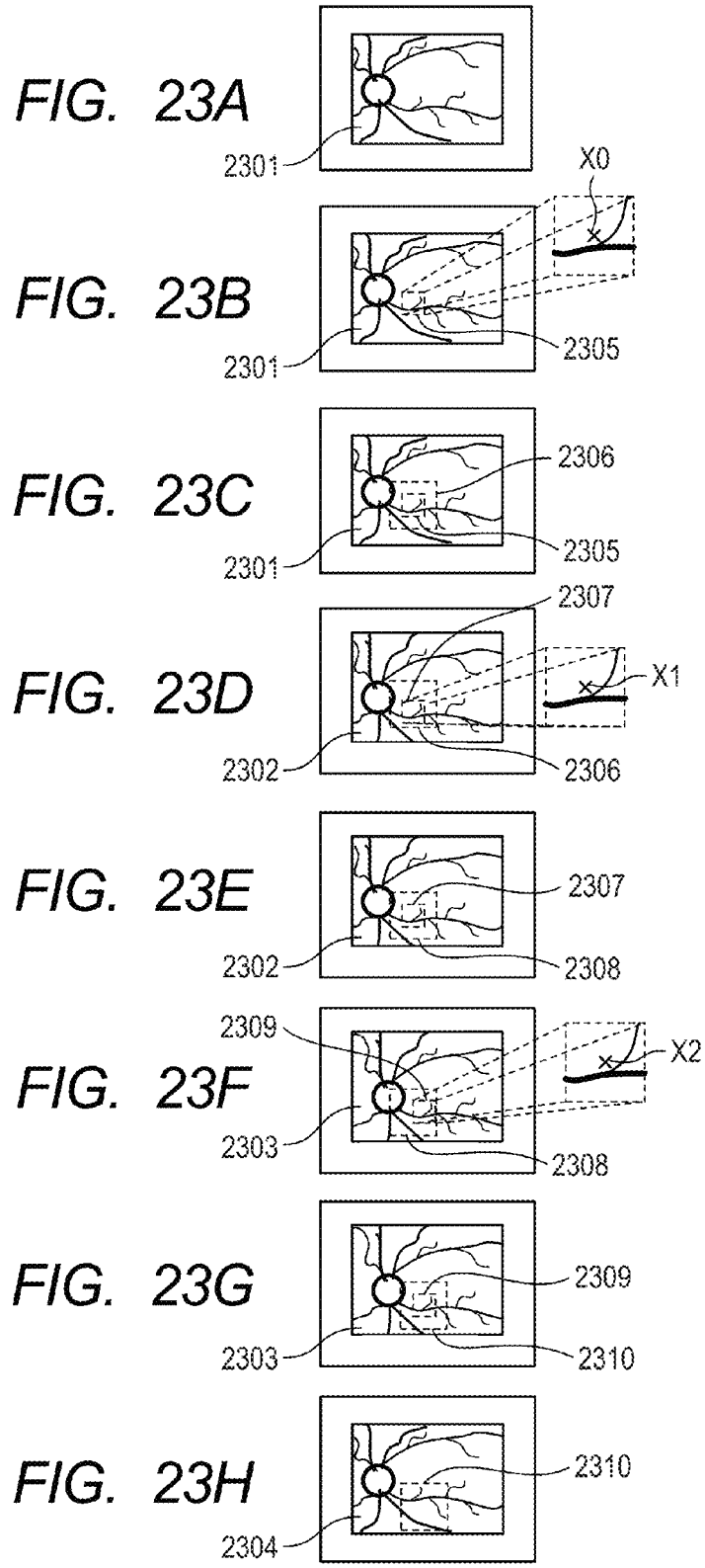
FIG. 23A is a schematic diagram illustrating an SLO fundus image in example 3 of the present invention.
FIG. 23B is a schematic diagram illustrating an SLO fundus image in example 3 of the present invention.
FIG. 23C is a schematic diagram illustrating an SLO fundus image in example 3 of the present invention.
FIG. 23D is a schematic diagram illustrating an SLO fundus image in example 3 of the present invention.
FIG. 23E is a schematic diagram illustrating an SLO fundus image in example 3 of the present invention.
FIG. 23F is a schematic diagram illustrating an SLO fundus image in example 3 of the present invention.
FIG. 23G is a schematic diagram illustrating an SLO fundus image in example 3 of the present invention.
FIG. 23H is a schematic diagram illustrating an SLO fundus image in example 3 of the present invention.

First, FIG. 23A illustrates a fundus image 2301 (first fundus image) acquired by the SLO. As illustrated in FIG. 23B, a template image 2305 including blood vessels is extracted from the acquired SLO image 2301. Center coordinates X0 of the extracted template image are stored. A matching region is set according to the rate of SLO image acquisition, i.e., 30 Hz. Referring to FIG. 9, a matching region 2306 is set as illustrated in FIG. 23C, considering 100 µm, which is the eye movement distance for 1/30 seconds, which are the time required for one SLO image to be acquired.

Next, as illustrated in FIG. 23D, a new SLO image 2302 (second fundus image) is acquired. Template matching is performed for an extracting region (first extracting region) in the SLO image 2302, which corresponds to the matching region 2306 set in FIG. 23C. A region 2307 corresponding to the template image is detected, and coordinates X1 thereof are acquired. Furthermore, as illustrated in FIG. 23E, with the reference coordinates (center coordinates in the present example) X1 of the region corresponding to the template image as the center and in consideration of the eye movement distance of 100 µm, a next matching region 2308 is set. Independently from the setting of the matching region, the eye movement amount is calculated from the coordinate values of coordinates X0 and X1. The calculation results are fed back to scanners in the OCT apparatus.

As illustrated in FIG. 23F, a new SLO image 2303 is acquired. Template matching is performed for an extracting region (second extracting region) in the SLO image 2303, which corresponds to the matching region 2308 set in FIG. 23E. A region 2309 corresponding to the template image is detected, and reference coordinates (center coordinates in the present example) X2 of the region corresponding to the template image are acquired. Furthermore, as illustrated in FIG. 23G, with the coordinates X2 as the center and in consideration of the eye movement distance of 100 µm, a next matching region 2310 is set. Independently from the setting of the matching region, the eye movement amount is calculated from the coordinate values of the coordinates X1 and X2.

Although a description of the subsequent processing will be omitted, processing for further acquiring a new SLO image 2304 as illustrated in FIG. 23H, performing template matching for a region in the SLO image 2304 corresponding to the matching region 2310, detecting a region corresponding to the template image, acquiring reference coordinates thereof, and setting a new matching region is repeated until the end of the OCT imaging.

As described above, a matching region is set for each acquired SLO image according to the rate of SLO image acquisition, and applied to an SLO image acquired next, enhancing the feedback speed. Furthermore, during OCT imaging, the amount of movement of an eyeball is calculated from the SLO images and fed back to the OCT apparatus, thereby acquiring an OCT image while moving a region scanned with OCT scan according to the eye movement amount, enabling provision of a high-quality OCT image.

Although in the preceding examples, one characteristic image is extracted to figure out a movement amount, it is possible that: a plurality of characteristic images is extracted, and an average value of respective movement amounts obtained as a result of pattern matching being performed based on the respective characteristic images is fed back to the OCT apparatus.

Example 4

Example 4 of the present invention will be described.

Control Method

A fundus camera is used for fundus image acquisition. The configuration and functional architecture of a used apparatus are similar to those in example 1, and thus, an overlapping description thereof will be omitted.

Figure 24:
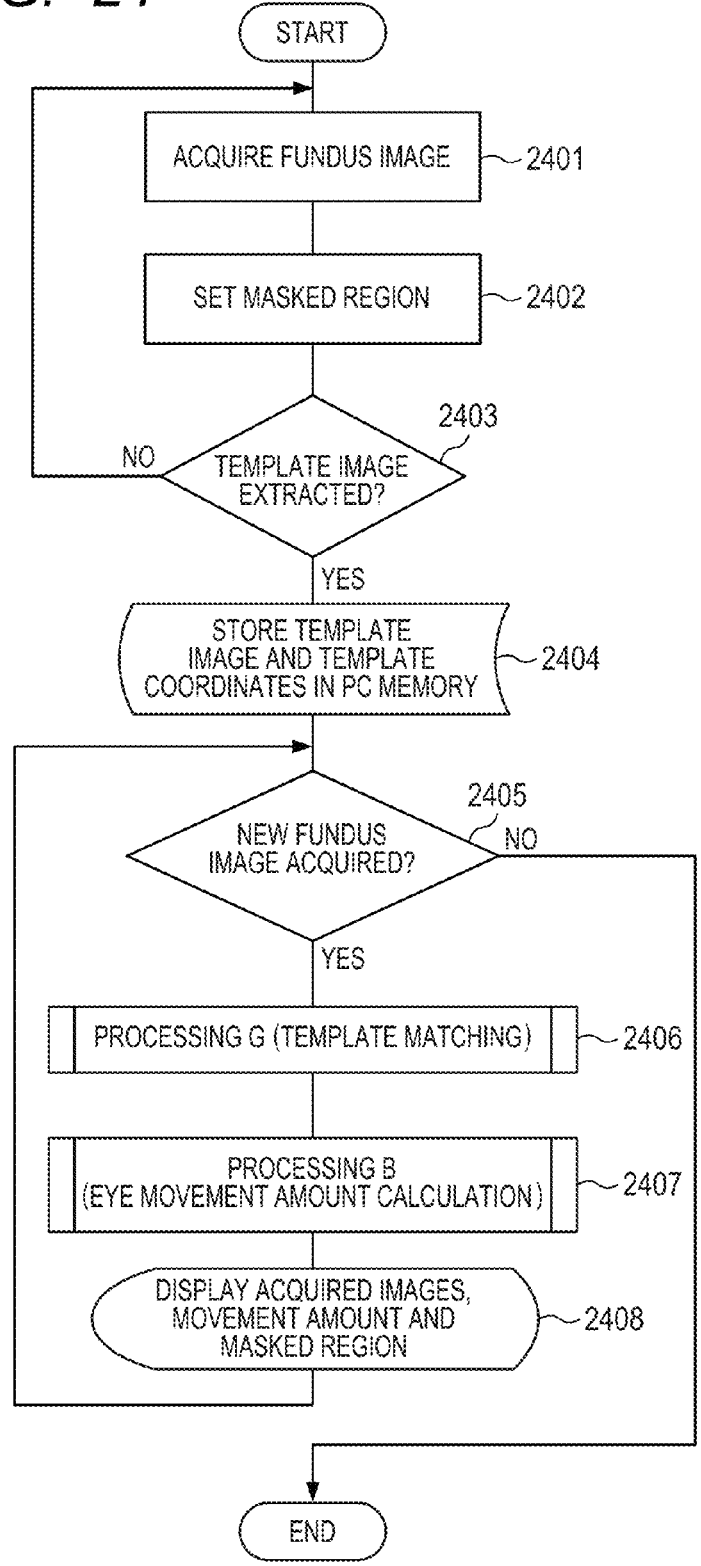
FIG. 24 is a flowchart of a control flow in example 4 of the present invention.

FIG. 24 illustrates an overall flow of measuring eye movements for a fixed period of time using the above-described functions. A first fundus image is acquired using a fundus camera 1 (step 2401). After the acquisition of the first fundus image, before extraction of a characteristic image (template), a region having a fixed width from a peripheral portion of the first image toward center coordinates of the image is set as a masked region (first region) (step 2402). Here, the masked region is set so that the width of the masked region is broader than a distance in which an eyeball moves as a result of, e.g., involuntary eye movements within measurement time. With the portion other than the masked region as an extracting region (second region), a template image is extracted from the extracting region (step 2403). There is no specific limitation on the method for extracting a template image as long as the method is a characteristic image extraction method enabling search and detection between a plurality of images. The template image, information on a reference position set in the first image, and information on template coordinates are stored in a recording unit 204 (step 2404). Since the fundus camera performs imaging successively for the fixed period of time, a following new fundus image (second fundus image) is acquired (step 2405). In processing G (step 2406), the entire acquired second fundus image is searched for the template image (template matching). In processing B, a position change of the template image is calculated and the eye movement amount for the fixed period of time is calculated (step 2407). The above-described processing from steps 2405 to 2407 is repeated until the end of measurement of eye movements (a new image is acquired). Also, the eye movement amount, the image, the measurement time and real-time monitor image of an anterior eye part, etc., may be displayed on a display 202 (step 408).

Figure 25:
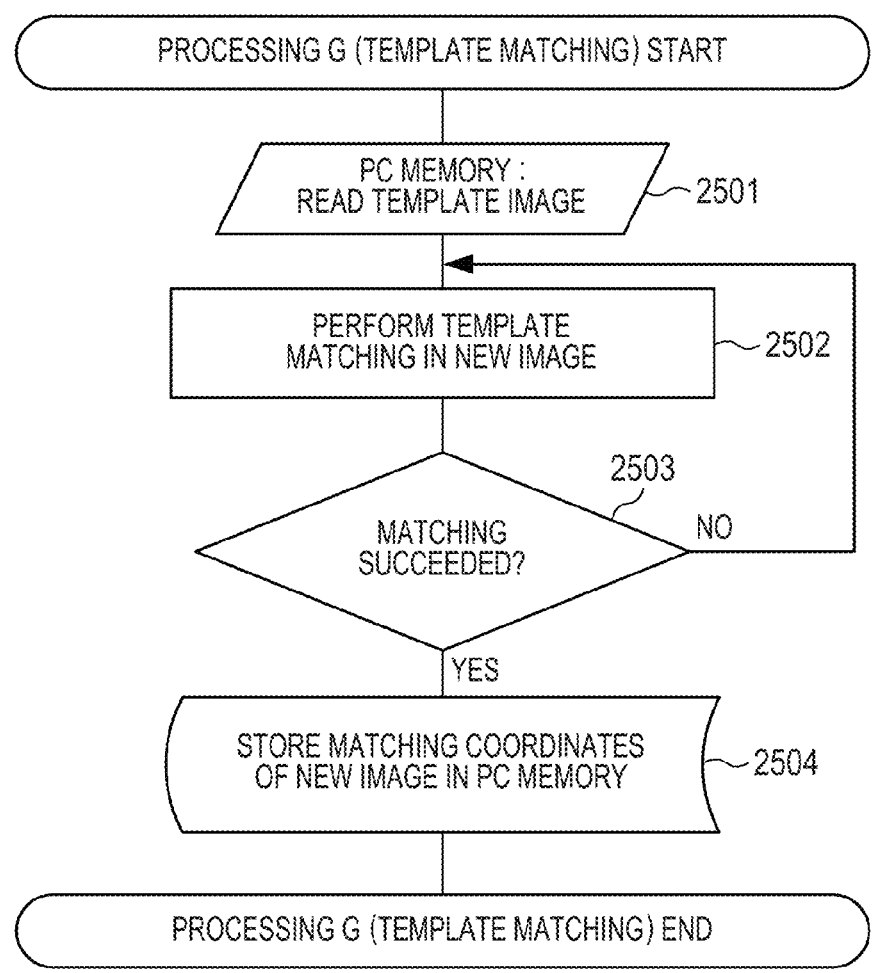
FIG. 25 is a flowchart relating to processing G in the control flow in example 4 of the present invention.

Processing G (step 2406), which is a partial flow, will be described with reference to FIG. 25. In template matching, the template image stored in the recording unit 204 is read (step 2501) and template matching is performed for a newly-acquired fundus image (step 2502). A method to be employed for template matching is not limited and the template matching may also be performed by means of any known method. After the template matching (step 2503), matching coordinates are stored in the recording unit 204. Since processing B is similar to that in example 1, an overlapped description thereof will be omitted.

Tracking Measurement: Specific Example

FIGS. 26A, 26B, 26C, 26D, 26E, 26F and 26G illustrate a specific example in which the respective processing steps described above are performed for acquired fundus images. Using the above-described fundus camera 1, tracking measurement is performed on a fundus for ten seconds under measurement conditions of acquiring a fundus image with a diameter of 10 mm at a frequency of 10 Hz.

Figure 26A:
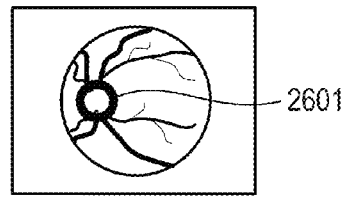
FIG. 26A is a schematic diagram illustrating a fundus image in example 4 of the present invention.
Figure 26B:
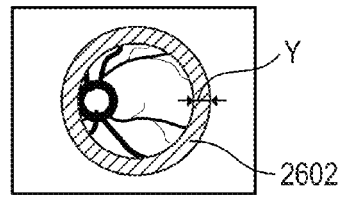
FIG. 26B is a schematic diagram illustrating a fundus image in example 4 of the present invention.
Figure 26C:
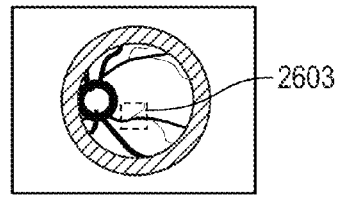
FIG. 26C is a schematic diagram illustrating a fundus image in example 4 of the present invention.
Figure 26D:
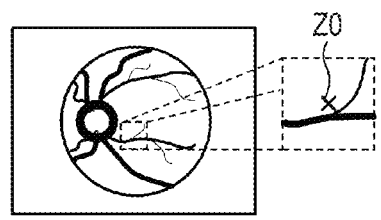
FIG. 26D is a schematic diagram illustrating a fundus image in example 4 of the present invention.
Figure 26E:
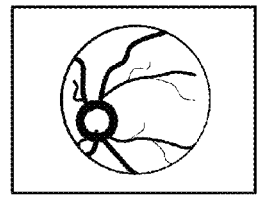
FIG. 26E is a schematic diagram illustrating a fundus image in example 4 of the present invention.
Figure 26F:
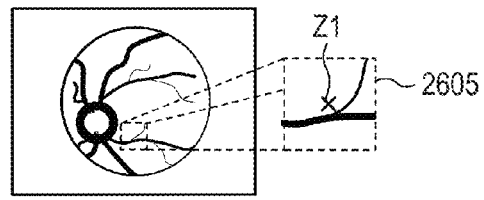
FIG. 26F is a schematic diagram illustrating a fundus image in example 4 of the present invention.
Figure 26G:
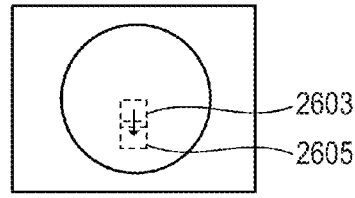
FIG. 26G is a schematic diagram illustrating a fundus image in example 4 of the present invention.

First, FIG. 26A illustrates an acquired first digital fundus image. As illustrated in FIG. 26A, blood vessels run intricately from a papilla 2601 toward an edge portion. After the acquisition of the first fundus image, as illustrated in FIG. 26B, a region of Y=600 μm from the edge portion of the image is set as a masked region 2602. A method for setting the width Y of the masked region will be described later. A template image 2603, which is indicated by dotted lines in FIG. 26C, is extracted from an extracting region other than the masked region with arrangement made not to extract a template from the masked region 2602. Although here, a template image has a square shape with a size of 500 μm×500 μm, the template image is not limited to this and the shape and size of the template image can arbitrarily be determined. In the present example, where center coordinates of a fundus photo is an origin (0, 0), center coordinates (template coordinates) of the template image extracted from the first fundus image, which are illustrated in FIG. 26D, are $Z_0$ (0, −200). Here, the coordinate unit is μm. Next, FIG. 26E, which is an object second fundus image, is searched for the template. As illustrated in FIG. 26F, after template matching being performed, matching coordinates $Z_1$ of a matching image 2605 corresponding to the template image are measured. In this example, the matching coordinates $Z_1$ are (0, −400). As illustrated in FIG. 26G, a coordinate change is figured out from the template coordinates $Z_0$ and the matching coordinates $Z_1$ and the eye movement amount ((0 μm, −200 μm) in the present example) is calculated. The above-described template matching in FIGS. 26E to 26G is repeated in a manner similar to the above for third, fourth and onward fundus image figures acquired at 10 Hz, and the amount of movement of the eyeball from a reference position during measurement is measured and displayed.

An example of the method for setting a masked region, which has been performed in FIG. 26B, will be described below. As illustrated in FIG. 26B, in consideration of the size and precision of fundus images and attribute information such as a distance in which an eyeball moves as result of involuntary eye movements within measurement time during which all the fundus images are captured (ten seconds in the present example), an area having a width of Y mm from the peripheral portion of the image is designated as a masked region. In this case, the diameter of the image is 10 mm and the precision is around 10 μm. Also, an amount of movement of a human eye within measurement time can be figured out according to the graph in FIG. 9. For this graph, a known graph provided in advance for each imaging condition, such as external fixation, internal fixation, affected eye or normal subject, age, or time required for capturing one fundus image, can be used, and thus, the graph can arbitrary be selected depending on the measurement method and/or object. Involuntary eye movements of a normal subject using the present external fixation lamp amount to around 600 μm in measurement time of ten seconds. Accordingly, under the aforementioned conditions, a region with a width of 600 μm from the peripheral portion of the image has been secured as a masked region.

This masked region is a region that may fall outside the measurement area depending on the movement of the human eye during measurement. Accordingly, as described above, a masked region 202 is set when a template is extracted, avoiding the template image from falling outside the area of an acquired image due to movements of a human eye during measurement, preventing a template detection error and enabling stable measurement of eye movements.

Example 5

Example 5 of the present invention will be described below.

Example 5 will be described in terms of a case where an SLO is used for fundus image acquisition, eye movements are measured from the SLO fundus images by means of a method similar to that of example 4, and the results of measurement of the eye movements are fed back in real time to an OCT apparatus, thereby providing a high-precision stereoscopic OCT image.

The configuration and functional architecture of an ophthalmologic apparatus used in the present example is similar to those of example 2, and thus, an overlapping description thereof will be omitted.

Figure 27:
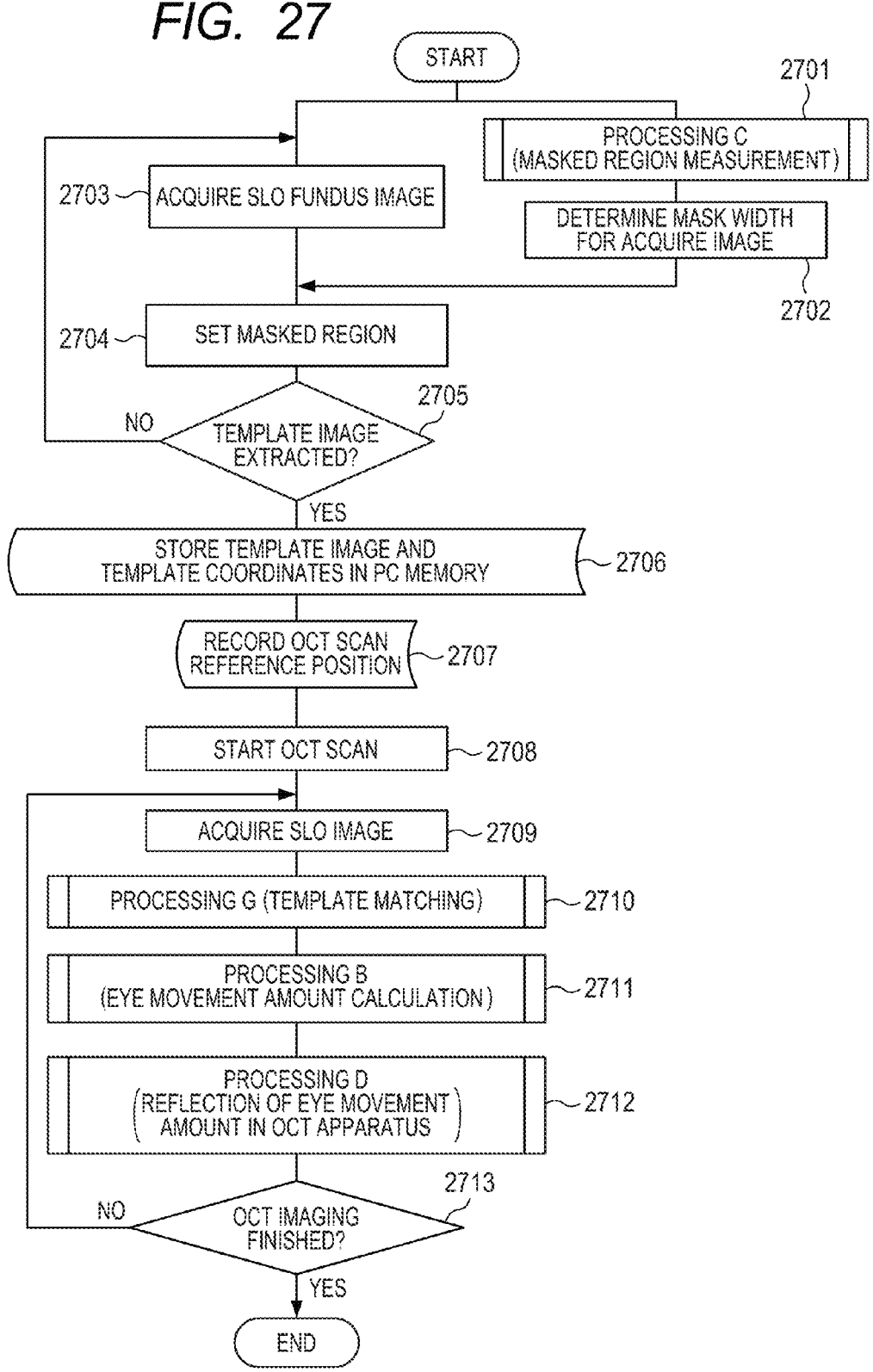
FIG. 27 is a flowchart of a control flow in example 5 of the present invention.

FIG. 27 illustrates an overall flow of measuring eye movements during acquiring tomographic images of an eyeball by means of an OCT apparatus using the above-described functions.

First, processing C (eye movement distance calculation) is performed (step 2701), and the width of a masked region is determined so as to be broader than a distance in which the eyeball moves as a result of, e.g., involuntary eye movements within measurement time (step 2702). Independently from the above processing, an SLO apparatus is activated and a fundus image is acquired by means of the SLO (step 2703). For the SLO image, a masked region (first region) is set from a peripheral portion of the first image toward center coordinates of the image (step 2704), and a template is extracted from an extracting region (second region), which is a region other than the masked region (step 2705). After the extraction of the template, the image, which is template information, and template coordinates, which are center coordinates of the template image, are stored (step 2706). A scan reference position of the OCT apparatus is stored (step 2707) and measurement by means of the OCT apparatus is started (step 2708). After acquisition of a new image from the SLO apparatus (step 2709), as in example 4, processing G (template matching) (step 2710) and processing B (eye movement amount calculation) are performed (step 2711), processing D (feedback of the eye movement amount to the OCT) is performed (step 2712), and during the OCT apparatus continuing measuring tomographic images, the process from steps 2709 to 2712 is repeated (step 2713).

After the end of OCT imaging, the measurement of eye movements is terminated (step 2714). Processing G and processing B are similar to those in example 4, and thus, a description thereof will be omitted.

Processing C (eye movement distance calculation: step 2701), which is a partial flow, is similar to processing C in example 2, and thus, an overlapping description will be omitted.

Processing D (feedback to the OCT apparatus: step 2712) is also similar to processing D in example 2, and thus, an overlapping description will be omitted. In the present example, a matching region may be displayed instead of displaying a masked region in step 1506.

Tracking Measurement: Specific Example

FIGS. 28A, 28B, 28C, 28D, 28E, 28F and 28G illustrate a specific example in which the respective above-described processing steps are performed for SLO images acquired when measuring a normal eye using an apparatus including an internal fixation lamp. The L-SLO has a line width of 10 mm and a scan range of 10 mm, that is, a size of an image for a fundus position is 10 mm×10 mm. SLO images can be acquired at a frequency of 30 Hz. For conditions for acquiring OCT images, the above-described SD-OCT is used, a camera is made to operate at a rate of 70 k A-scans, a B-scan image (with a fundus scan range of 10 mm, and a laser spot diameter of 20 μm) includes 1000 lines, and a 3D image of a retina including 280 B-scan images is acquired. The measurement time amounts to four seconds.

Figure 28A:
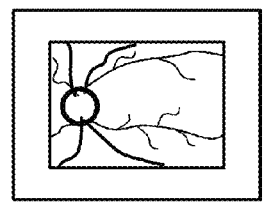
FIG. 28A is a schematic diagram illustrating an SLO image in example 5 of the present invention.
Figure 28B:
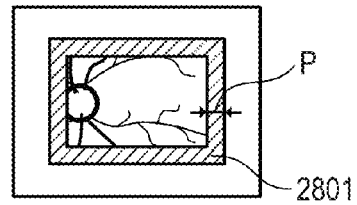
FIG. 28B is a schematic diagram illustrating an SLO image in example 5 of the present invention.
Figure 28C:
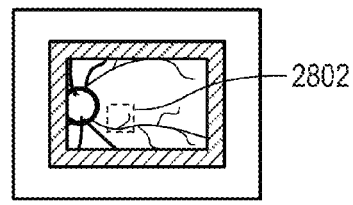
FIG. 28C is a schematic diagram illustrating an SLO image in example 5 of the present invention.
Figure 28D:
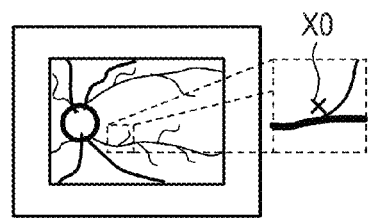
FIG. 28D is a schematic diagram illustrating an SLO image in example 5 of the present invention.
Figure 28E:
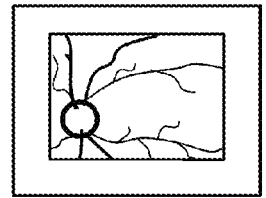
FIG. 28E is a schematic diagram illustrating an SLO image in example 5 of the present invention.
Figure 28F:
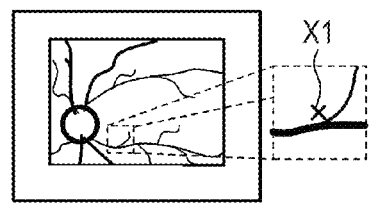
FIG. 28F is a schematic diagram illustrating an SLO image in example 5 of the present invention.
Figure 28G:
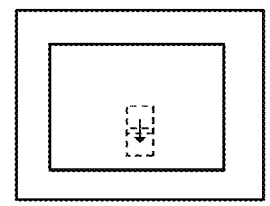
FIG. 28G is a schematic diagram illustrating an SLO image in example 5 of the present invention.

FIG. 28A illustrates a fundus image (SLO image) acquired in the SLO. As illustrated in FIG. 28A, blood vessels run intricately from a papilla toward an edge portion. After the acquisition of the first SLO image, the measurement time (four seconds in the present example) is calculated from the OCT imaging conditions. Referring to FIG. 9, an eyeball moves 470 μm in four seconds, and thus, as illustrated in FIG. 28B, a region of P=470 μm from the edge portion of the image is set in a masked region 2801 and a template image 2802 with a size of 500 μm×500 μm such as indicated by dotted lines in FIG. 28C is extracted with arrangement made not to extract a template from the masked region 2801. Although here, the template image has a square shape with a size of 500 μm×500 μm, the template image according to the present invention is not limited to this, and the shape and size of the template image may arbitrarily be determined. After the extraction of the template, template coordinates $X_0$ in FIG. 28D is set as a reference for movement amount calculation. In the present example, where center coordinates of the SLO image is an origin (0, 0), template coordinates of this template image were $X_0$ (−50, −200). The coordinate unit is μm. Next, template matching is performed for FIG. 28E, which is a next object second fundus image. As illustrated in FIG. 28F, after the template matching being performed, matching coordinates $X_1$ of a matched matching image are measured. In this second fundus image figure, the matching coordinates were $X_1$ (−50, −400). As illustrated in FIG. 28G, coordinate changes are obtained from the template coordinates $X_0$ and the matching coordinates $X_1$ to calculate the eye movement amount (0 μm, −200 μm). The results of the above-described calculation are reflected in scanners 1105 and 1108 in the OCT apparatus via a CPU, whereby the scan position of the OCT is changed. The above-described template matching from FIGS. 28E to 28G is repeated: matching is performed for each of SLO images acquired at a frequency of 30 Hz, and fed back to the OCT apparatus. In the present example, during the above processing, as illustrated in FIG. 19, an OCT image 1901, eye movement measurement results 1906, remaining measurement time 1905, an SLO image (including indication of a masked region and a template image) 1904, imaging conditions 1908, etc., may be displayed on a display 1907 to enable a user to confirm the operation.

A method for setting a masked region such as illustrated in FIG. 28B will be described below. Inspection time for inspection using an ophthalmologic apparatus (the OCT apparatus in the present example) that is different from a fundus imaging unit is calculated. From the inspection time and the imaging conditions, a graph in FIG. 9 matching the imaging conditions, for example, external fixation, internal fixation, affected eye or normal subject, age, or time required for capturing one fundus image, is selected, and from the selected graph, the amount of movement of the eyeball is calculated. A masked region is determined with the amount of movement of the eyeball made to be the width of the masked region P.

This masked region is a region that may fall outside a measurement area due to movements of a human eye during measurement. Accordingly, setting a masked region 2802 for template extraction according to the OCT imaging time as described above avoids a template image from falling outside the area of an acquired image due to movements of a human eye during measurement, preventing a template detection error and enabling provision of a stereoscopic OCT image without image displacements caused by eye movements.

Example 6

In examples 4 and 5, a region where a masked region is set is not limited to a peripheral portion of an image, and a masked region may be set in, for example, a center portion of an acquired first fundus image.

Here, a masked region may be set in only a center portion of an image, or may also be set in both of a peripheral portion and a central portion of an image.

Figure 29:
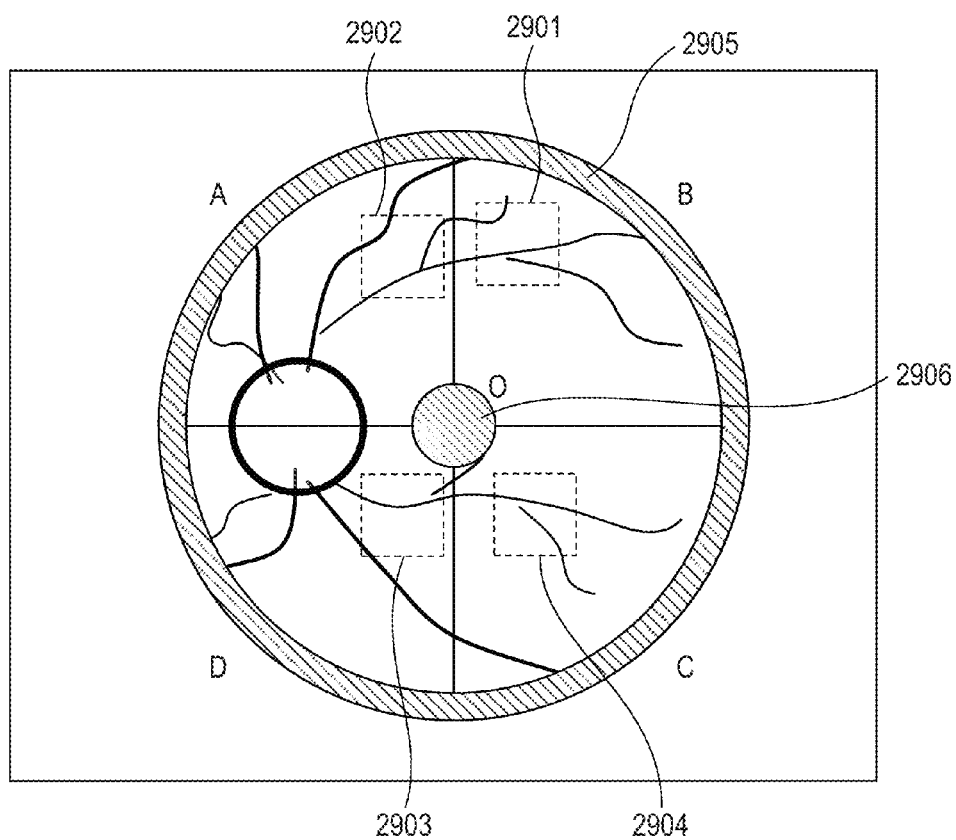
FIG. 29 is a schematic diagram indicating a fundus image in example 6 of the present invention.

For detecting a rotation of an eye ball, a plurality of characteristic images may be extracted from a first fundus image as illustrated in FIG. 29. Here, as in examples 4 and 5, a masked region (first region) is set so as to extend from a peripheral portion of the image as indicated by a shaded portion 2905. Furthermore, a masked region is also set in a center portion 2906 of the image. Here, the center portion can be defined as, for example, a region defined by a circle with a center of the first fundus image as its center, the region having a diameter that is larger than a distance in which an eyeball moves during the time of imaging all fundus images. In the present example, a radius of the circuit is set to be a value that is larger than the amount of movement of an eyeball because when the respective characteristic images move over the center, it is difficult to distinguish among a rotation movement, a shift of an eyeball and a magnification of the eye ball (movement in the eye axis direction) from each other. Even if the radius is smaller than the amount of movement of the eyeball, an adjustment can be made by means of measurement conditions (changing the number and/or size of characteristic images, and/or the method for extraction of characteristic images). As in examples 4 and 5, a distance in which an eyeball moves can be figured out from a graph indicating a function modeling a relationship between time from the start of fixation and an amount of movement of a human eye. Also, similarly, a known graph provided in advance for each imaging condition, such as external fixation, internal fixation, affected eye or normal subject, age, or time required for capturing one fundus image, can be used, and thus, the graph can arbitrary be selected depending on the measurement method and/or subject.

If a characteristic image is extracted from the masked region, no coordinate difference due to the rotation of the eyeball may be caused between template coordinates and matching coordinates, disabling measurement of the rotation. Accordingly, setting the masked region 2906 for extracting the template according to the imaging time as described above can prevent extraction of a template from the center portion of the image, enabling more reliable detection of a rotation movement of the eyeball.

Then, after the determination of the mask, the image is divided into four parts as indicated by A, B, C and D, and characteristic images 2901, 2902, 2903 and 2904 are extracted from respective areas resulting from the division. Subsequently, as in examples 1 and 2, distances of movements of the respective characteristic images 2901, 2902, 2903 and 2904 are detected and the rotation of the eyeball is calculated from the four points.

As described above, extraction of characteristic images from an image other than enables correct calculation of a rotation of an eyeball. Although in the present example, a circular image as in example 1 has been used, similar processing can be performed with a rectangular fundus image as in example 2.

Others

Although the respective examples have individually been described, two or more of the examples may be combined (for example, a matching region and a masked region may be set at the same time).

Although in each of the above examples, extraction is performed using a template image of blood vessels, an effect similar to those in the examples can be obtained using a template image of a macula or a papilla. For fundus image acquisition, fundus images may be acquired using an imaging system other than those used in the examples, such as a fundus camera, a scan laser ophthalmoscope (SLO) and an optical coherence tomographic imaging apparatus. Furthermore, an effect similar to those in the examples can be provided using, e.g., a visual field test apparatus for conducting a visual field test.

Furthermore, in the case of using, e.g., blood vessels, in order to detect a rotation of an eyeball, a plurality of characteristic images may be extracted. In such case, also, an effect similar to those in the examples can be provided by setting a matching region and an extracting region for each of the characteristic images.

The sequences in the flows indicated in examples 1 to 6 are not limited to these, and an effect similar to those provided by the present invention can be provided even if a sequence different from those in examples 1 to 6 is provided or another flow is provided. Also, although center coordinates are used for reference coordinates for calculating a movement amount, an effect similar to that case can be provided using edge coordinates or coordinates in crossing of blood vessels.

Although in examples 1 and 4, a matching region is set to 700 μm and a masked region is set to 600 μm because an internal fixation lamp is provided, a width set for a matching region/masked region can arbitrarily be set according to various circumstances such as imaging conditions for fundus images. For example, where fixation is more stable, a matching region/masked region can be reduced in size, while where fixation is unstable as in the case of, e.g., an older person or an affected eye, a matching region/masked region can favorably be increased in size. Also, as an imaging condition, time required for capturing one fundus image may be taken into consideration. Where measurement is performed a plurality of times for a same test object, a more accurate matching region/masked region can be set by using measurement data in the previous measurements, enabling an increase in speed of template matching. Although in the present example, a region obtained as a result of extending all the peripheral sides of a template image by a same value $R_1$ is set as a matching region, an effect similar to those in the examples can be provided if values differing depending on the extension directions are employed according to the amount of movement of a human eye during measurement time. Similarly, the width of the masked region may have different values in the respective directions according to the amount of movement of a human eye.

Although in examples 1 to 6, corrections for eye movements have been made in real time for an ophthalmologic apparatus, an effect is also exerted where correction or post-processing is performed on an acquired image after the end of measurement.

For the graph in FIG. 9 for calculating an eye movement amount, a more accurate movement amount can be calculated by using a different graph depending on the conditions, such as external fixation/internal fixation, affected eye/normal subject, age, individual, enabling provision of a more accurate matching region and mask region.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

REFERENCE SIGNS LIST

1: fundus camera body portion
50: digital single-lens reflex camera
602: matching region
$R_1$: matching region setting width
1002: extracting region
2602: masked region
2802: masked region
Y: masked region setting width
2906: masked region This application claims the benefit of Japanese Patent Applications No. 2010-056545, filed Mar. 12, 2010, No. 2010-056557, filed Mar. 12, 2010, and No. 2010-243537, filed Oct. 29, 2010, which are hereby incorporated by reference herein in their entirety.

The invention claimed is:

1. An ophthalmologic apparatus comprising:
an image acquiring unit configured to acquire a plurality of fundus images of an eye to be inspected, at different times;
a processing unit configured to extract at least one characteristic region in a region other than a partial region having a predetermined width from a peripheral portion in at least one fundus image among the plurality of fundus images; and
a measurement unit configured to measure a movement of the eye by using the at least one characteristic region.

2. An ophthalmologic apparatus according to claim 1, wherein the processing unit includes an extracting unit configured to extract a characteristic region in the region other than the partial region, and a searching unit configured to search a region corresponding to the extracted characteristic region in at least one fundus image which is not the fundus image in which the characteristic region is extracted, among the plurality of fundus images.

3. An ophthalmologic apparatus according to claim 1, wherein the image acquiring unit acquires the plurality of fundus images based on return light from the eye to be inspected irradiated with measuring light through a scanning unit, and includes a control unit configured to control the scanning unit based on a positional displacement on the plurality of fundus images.

4. An ophthalmologic apparatus according to claim 3, wherein the control unit sequentially causes the processing unit, the measurement unit, the scanning unit, and the acquiring unit to operate.

5. An ophthalmologic apparatus according to claim 1, wherein the processing unit extracts the at least one characteristic region in the region other than the partial region having the predetermined width from four sides of the at least one fundus image among the plurality of fundus images.

6. An ophthalmologic apparatus according to claim 1, wherein the at least one characteristic region includes an image of at least one of a branching and a crossing of a blood vessel in the fundus.

7. An ophthalmologic apparatus according to claim 1, wherein the image acquiring unit includes any of a fundus camera, a scanning laser ophthalmoscope, an optical coherence tomographic imaging apparatus, and a visual field test apparatus.

8. An ophthalmologic apparatus according to claim 1, wherein the plurality of fundus images includes a plurality of SLO images, and wherein the apparatus further comprises a unit configured to acquire a plurality of OCT images respectively corresponding to the plurality of SLO images.

9. An ophthalmologic apparatus according to claim 1, further comprising a display control unit configured to control a display unit to display a display form designating an amount of the measured movement of the eye.

10. An ophthalmologic apparatus comprising:
an image acquiring unit configured to acquire a plurality of fundus images of an eye to be inspected, at different times;
a determining unit configured to determine a partial region having a predetermined width from a peripheral portion in at least one fundus image among the plurality of fundus images;
a processing unit configured to extract at least two characteristic regions in a region other than the determined partial region in at least two fundus images among the plurality of fundus images, and to calculate a difference between coordinates of the at least two characteristic regions; and
a measurement unit configured to measure a movement of the eye based on a result of an operation of the processing unit.

11. An ophthalmologic apparatus according to claim 10, wherein the processing unit includes an extracting unit configured to extract a characteristic region in the region other than the determined partial region, and a searching unit configured to search a region corresponding to the extracted characteristic region in at least one fundus image which is not the fundus image in which the characteristic region is extracted, among the plurality of fundus images.

12. An ophthalmologic apparatus according to claim 10, wherein the image acquiring unit acquires the plurality of fundus images based on return light from the eye to be inspected irradiated with measuring light through a scanning unit, and includes a control unit configured to control the scanning unit based on a positional displacement on the plurality of fundus images.

13. An ophthalmologic apparatus according to claim 12, wherein the control unit sequentially causes the processing unit, the measurement unit, the scanning unit, and the acquiring unit to operate.

14. An ophthalmologic apparatus according to claim 10, wherein the determining unit determines the partial region having the predetermined width from four sides of the at least one fundus image among the plurality of fundus images.

15. An ophthalmologic apparatus according to claim 10, wherein the characteristic region includes an image of at least one of a branching and a crossing of a blood vessel in the fundus.

16. A method for measuring a movement of an eye to be inspected, the method comprising the steps of:

acquiring a plurality of fundus images of an eye to be inspected at different times;

extracting at least one characteristic region in a region other than a partial region having a predetermined width from a peripheral portion in the at least one fundus image in at least one fundus image among the plurality of fundus images; and measuring a movement of the eye by using the at least one characteristic region.

17. A non-transitory tangible medium having recorded thereon a program for causing a computer to perform steps of the method according to claim 16.

18. A method for measuring a movement of an eye to be inspected, the method comprising the steps of:

acquiring a plurality of fundus images of an eye to be inspected at different times;

determining a partial region having a predetermined width from a peripheral portion in at least one fundus image among the plurality of fundus images;

extracting at least two characteristic regions in a region other than the determined partial region in at least two fundus images among the plurality of fundus images;

calculating a difference between coordinates of the at least two characteristic regions; and measuring a movement of the eye based on a result of the calculated difference.

19. A non-transitory tangible medium having recorded thereon a program for causing a computer to perform steps of the method according to claim 18.

* * * * *